(12) United States Patent
Creighton, IV et al.

(10) Patent No.: US 7,966,059 B2
(45) Date of Patent: Jun. 21, 2011

(54) ROTATING AND PIVOTING MAGNET FOR MAGNETIC NAVIGATION

(75) Inventors: Francis M. Creighton, IV, St. Louis, MO (US); Seth Burgett, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 1104 days.

(21) Appl. No.: 11/699,003

(22) Filed: Jan. 26, 2007

(65) Prior Publication Data

US 2007/0146106 A1 Jun. 28, 2007

Related U.S. Application Data

(63) Continuation of application No. 10/946,634, filed on Sep. 21, 2004, now Pat. No. 7,313,429, which is a continuation-in-part of application No. 10/347,525, filed on Jan. 17, 2003, now Pat. No. 7,019,610, which is a continuation-in-part of application No. 10/056,227, filed on Jan. 23, 2002, now Pat. No. 6,975,197, application No. 11/699,003, which is a continuation of application No. 10/796,568, filed on Mar. 9, 2004, now Pat. No. 7,264,584, which is a continuation of application No. 09/678,640, filed on Oct. 3, 2000, now Pat. No. 6,702,804.

(60) Provisional application No. 60/157,619, filed on Oct. 4, 1999.

(51) Int. Cl.
*A61B 6/00* (2006.01)
(52) U.S. Cl. ........................................ 600/427; 128/899
(58) Field of Classification Search .......... 600/424–427; 335/296–306; 128/899
See application file for complete search history.

(56) References Cited

U.S. PATENT DOCUMENTS

| | | | |
|---|---|---|---|
| 4,608,992 A | 9/1986 | Hakim et al. | 600/431 |
| 4,671,287 A | 6/1987 | Fiddian-Green | 600/363 |
| 5,049,151 A | 9/1991 | Durham et al. | 606/98 |
| 5,257,636 A | 11/1993 | White | |
| 5,312,321 A | 5/1994 | Holcomb | |
| 5,380,268 A | 1/1995 | Wheeler | 600/30 |
| 5,622,169 A | 4/1997 | Golden et al. | |
| 5,654,864 A | 8/1997 | Ritter et al. | |
| 5,667,469 A | 9/1997 | Zhang et al. | 600/9 |
| 5,681,260 A | 10/1997 | Ueda et al. | |
| 5,693,091 A | 12/1997 | Larson et al. | 623/3.27 |
| 5,735,278 A | 4/1998 | Hoult et al. | 600/422 |
| 5,900,793 A | 5/1999 | Katznelson et al. | 335/296 |
| 5,931,818 A | 8/1999 | Werp et al. | |
| 5,980,246 A | 11/1999 | Ramsay et al. | 433/5 |
| 6,014,580 A | 1/2000 | Blume et al. | |
| 6,015,414 A | 1/2000 | Werp et al. | |
| 6,029,081 A | 2/2000 | DeMeester et al. | 600/410 |
| 6,128,174 A | 10/2000 | Ritter et al. | |
| 6,128,522 A | 10/2000 | Acker et al. | 600/411 |
| 6,148,823 A | 11/2000 | Hastings | |

(Continued)

*Primary Examiner* — Ramon M Barrera
(74) *Attorney, Agent, or Firm* — Harness, Dickey & Pierce, P.L.C.

(57) ABSTRACT

A system for magnetically navigating a medical device in an operating region within the body of a patient. The system includes a magnet having a front field projecting from the front of the magnet sufficient to project a magnetic field into the operating region in the patient. The magnet is mounted for movement between a navigation position in which the magnet is located adjacent to the patient with the front of the magnetic generally facing the operating region, and an imaging position in which the magnet is spaced from the patient and the front generally faces away from the operating region.

9 Claims, 38 Drawing Sheets

U.S. PATENT DOCUMENTS

| | | |
|---|---|---|
| 6,152,933 A | 11/2000 | Werp et al. |
| 6,157,281 A | 12/2000 | Katznelson et al. .......... 335/306 |
| 6,157,853 A | 12/2000 | Blume et al. |
| 6,212,419 B1 | 4/2001 | Blume et al. |
| 6,241,671 B1 | 6/2001 | Ritter et al. |
| 6,292,678 B1 | 9/2001 | Hall et al. |
| 6,296,604 B1 | 10/2001 | Garibaldi et al. |
| 6,298,257 B1 | 10/2001 | Hall et al. |
| 6,304,768 B1 | 10/2001 | Blume et al. |
| 6,315,709 B1 | 11/2001 | Garibaldi et al. |
| 6,317,618 B1 | 11/2001 | Livni et al. .................... 600/410 |
| 6,330,467 B1 | 12/2001 | Creighton, IV et al. |
| 6,352,363 B1 | 3/2002 | Munger et al. |
| 6,364,823 B1 | 4/2002 | Garibaldi et al. |
| 6,375,606 B1 | 4/2002 | Garibaldi et al. |
| 6,385,472 B1 | 5/2002 | Hall et al. |
| 6,401,723 B1 | 6/2002 | Garibaldi et al. |
| 6,428,551 B1 | 8/2002 | Hall et al. |
| 6,459,924 B1 | 10/2002 | Creighton, IV et al. |
| 6,475,223 B1 | 11/2002 | Werp et al. |
| 6,505,062 B1 | 1/2003 | Ritter et al. |
| 6,507,751 B2 | 1/2003 | Blume et al. |
| 6,522,909 B1 | 2/2003 | Garibaldi et al. |
| 6,524,303 B1 | 2/2003 | Garibaldi |
| 6,527,782 B2 | 3/2003 | Hogg et al. |
| 6,530,947 B1 | 3/2003 | Euteneuer et al. ........... 623/1.11 |
| 6,537,196 B1 | 3/2003 | Creighton, IV et al. |
| 6,542,766 B2 | 4/2003 | Hall et al. |
| 6,562,019 B1 | 5/2003 | Sell |
| 6,630,879 B1 | 10/2003 | Creighton, IV et al. |
| 6,662,034 B2 | 12/2003 | Segner et al. |
| 6,677,752 B1 | 1/2004 | Creighton, IV et al. |
| 6,702,804 B1 | 3/2004 | Ritter et al. |
| 6,733,511 B2 | 5/2004 | Hall et al. |
| 6,755,816 B2 | 6/2004 | Ritter et al. |
| 6,817,364 B2 | 11/2004 | Garibaldi et al. |
| 6,834,201 B2 | 12/2004 | Gillies et al. |
| 6,902,528 B1 | 6/2005 | Garibaldi et al. |
| 6,911,026 B1 | 6/2005 | Hall et al. |
| 6,940,379 B2 | 9/2005 | Creighton |
| 6,968,846 B2 | 11/2005 | Viswanathan |
| 6,975,197 B2 | 12/2005 | Creighton, IV |
| 6,980,843 B2 | 12/2005 | Eng et al. |
| 7,008,418 B2 | 3/2006 | Hall et al. |
| 7,010,338 B2 | 3/2006 | Ritter et al. |
| 7,019,610 B2 | 3/2006 | Creighton, IV et al. |
| 7,020,512 B2 | 3/2006 | Ritter et al. |
| 7,066,924 B1 | 6/2006 | Garibaldi et al. |
| 7,137,976 B2 | 11/2006 | Ritter et al. |
| 7,161,453 B2 | 1/2007 | Creighton, IV |
| 7,189,198 B2 | 3/2007 | Harburn et al. |
| 7,190,819 B2 | 3/2007 | Viswanathan |
| 7,211,082 B2 | 5/2007 | Hall et al. |
| 2001/0038683 A1 | 11/2001 | Ritter et al. |
| 2002/0019644 A1 | 2/2002 | Hastings et al. |
| 2002/0100486 A1 | 8/2002 | Creighton, IV et al. |
| 2002/0177789 A1 | 11/2002 | Ferry et al. |
| 2003/0125752 A1 | 7/2003 | Werp et al. |
| 2004/0002643 A1 | 1/2004 | Hastings et al. |
| 2004/0006301 A1 | 1/2004 | Sell et al. |
| 2004/0019447 A1 | 1/2004 | Shachar |
| 2004/0030244 A1 | 2/2004 | Garibaldi et al. |
| 2004/0064153 A1 | 4/2004 | Creighton, IV et al. |
| 2004/0068173 A1 | 4/2004 | Viswanathan |
| 2004/0133130 A1 | 7/2004 | Ferry et al. |
| 2004/0147829 A1 | 7/2004 | Segner et al. |
| 2004/0157082 A1 | 8/2004 | Ritter et al. |
| 2004/0158972 A1 | 8/2004 | Creighton, IV et al. |
| 2004/0186376 A1 | 9/2004 | Hogg et al. |
| 2004/0199074 A1 | 10/2004 | Ritter et al. |
| 2004/0249262 A1 | 12/2004 | Werp et al. |
| 2004/0249263 A1 | 12/2004 | Creighton, IV |
| 2004/0260172 A1 | 12/2004 | Ritter et al. |
| 2004/0267106 A1 | 12/2004 | Segner et al. |
| 2005/0004585 A1 | 1/2005 | Hall et al. |
| 2005/0020911 A1 | 1/2005 | Viswanathan et al. |
| 2005/0021063 A1 | 1/2005 | Hall et al. |
| 2005/0033162 A1 | 2/2005 | Garibaldi et al. |
| 2005/0043611 A1 | 2/2005 | Sabo et al. |
| 2005/0065435 A1 | 3/2005 | Rauch et al. |
| 2005/0096589 A1 | 5/2005 | Shachar |
| 2005/0113628 A1 | 5/2005 | Creighton et al. |
| 2005/0113812 A1 | 5/2005 | Viswanathan et al. |
| 2005/0119556 A1 | 6/2005 | Gillies et al. |
| 2005/0119687 A1 | 6/2005 | Dacey, Jr. et al. |
| 2005/0182315 A1 | 8/2005 | Ritter et al. |
| 2005/0256398 A1 | 11/2005 | Hastings et al. |
| 2005/0273130 A1 | 12/2005 | Sell |
| 2006/0004382 A1 | 1/2006 | Hogg et al. |
| 2006/0009735 A1 | 1/2006 | Viswanathan et al. |
| 2006/0025676 A1 | 2/2006 | Viswanathan et al. |
| 2006/0025679 A1 | 2/2006 | Viswanathan et al. |
| 2006/0025719 A1 | 2/2006 | Viswanathan et al. |
| 2006/0036125 A1 | 2/2006 | Viswanathan et al. |
| 2006/0036163 A1 | 2/2006 | Viswanathan |
| 2006/0036213 A1 | 2/2006 | Viswanathan et al. |
| 2006/0041178 A1 | 2/2006 | Viswanathan et al. |
| 2006/0041179 A1 | 2/2006 | Viswanathan et al. |
| 2006/0041180 A1 | 2/2006 | Viswanathan et al. |
| 2006/0041181 A1 | 2/2006 | Viswanathan et al. |
| 2006/0041245 A1 | 2/2006 | Ferry et al. |
| 2006/0058646 A1 | 3/2006 | Viswanathan |
| 2006/0061445 A1 | 3/2006 | Creighton, IV et al. |
| 2006/0074297 A1 | 4/2006 | Viswanathan |
| 2006/0079745 A1 | 4/2006 | Viswanathan |
| 2006/0079812 A1 | 4/2006 | Viswanathan |
| 2006/0094956 A1 | 5/2006 | Viswanathan |
| 2006/0100505 A1 | 5/2006 | Viswanathan |
| 2006/0114088 A1 | 6/2006 | Shachar |
| 2006/0116633 A1 | 6/2006 | Shachar |
| 2006/0144407 A1 | 7/2006 | Aliberto et al. |
| 2006/0144408 A1 | 7/2006 | Ferry |
| 2006/0145799 A1 | 7/2006 | Creighton, IV |
| 2006/0270915 A1 | 11/2006 | Ritter et al. |
| 2006/0270948 A1 | 11/2006 | Viswanathan et al. |
| 2006/0278248 A1 | 12/2006 | Viswanathan |
| 2007/0016010 A1 | 1/2007 | Creighton, IV et al. |
| 2007/0016131 A1 | 1/2007 | Munger et al. |
| 2007/0019330 A1 | 1/2007 | Wolfersberger |
| 2007/0021731 A1 | 1/2007 | Garibaldi et al. |
| 2007/0021742 A1 | 1/2007 | Viswanathan |
| 2007/0021744 A1 | 1/2007 | Creighton, IV |
| 2007/0030958 A1 | 2/2007 | Munger |
| 2007/0032746 A1 | 2/2007 | Sell |
| 2007/0038064 A1 | 2/2007 | Creighton, IV |
| 2007/0038065 A1 | 2/2007 | Creighton, IV et al. |
| 2007/0038074 A1 | 2/2007 | Ritter et al. |
| 2007/0038410 A1 | 2/2007 | Tunay |
| 2007/0040670 A1 | 2/2007 | Viswanathan |
| 2007/0043455 A1 | 2/2007 | Viswanathan et al. |
| 2007/0049909 A1 | 3/2007 | Munger |
| 2007/0055124 A1 | 3/2007 | Viswanathan et al. |
| 2007/0055130 A1 | 3/2007 | Creighton, IV |
| 2007/0060829 A1 | 3/2007 | Pappone |
| 2007/0060916 A1 | 3/2007 | Pappone |
| 2007/0060962 A1 | 3/2007 | Pappone |
| 2007/0060966 A1 | 3/2007 | Pappone |
| 2007/0060992 A1 | 3/2007 | Pappone |
| 2007/0062546 A1 | 3/2007 | Viswanathan et al. |
| 2007/0062547 A1 | 3/2007 | Pappone |
| 2007/0073288 A1 | 3/2007 | Hall et al. |
| 2007/0088197 A1 | 4/2007 | Garibaldi et al. |

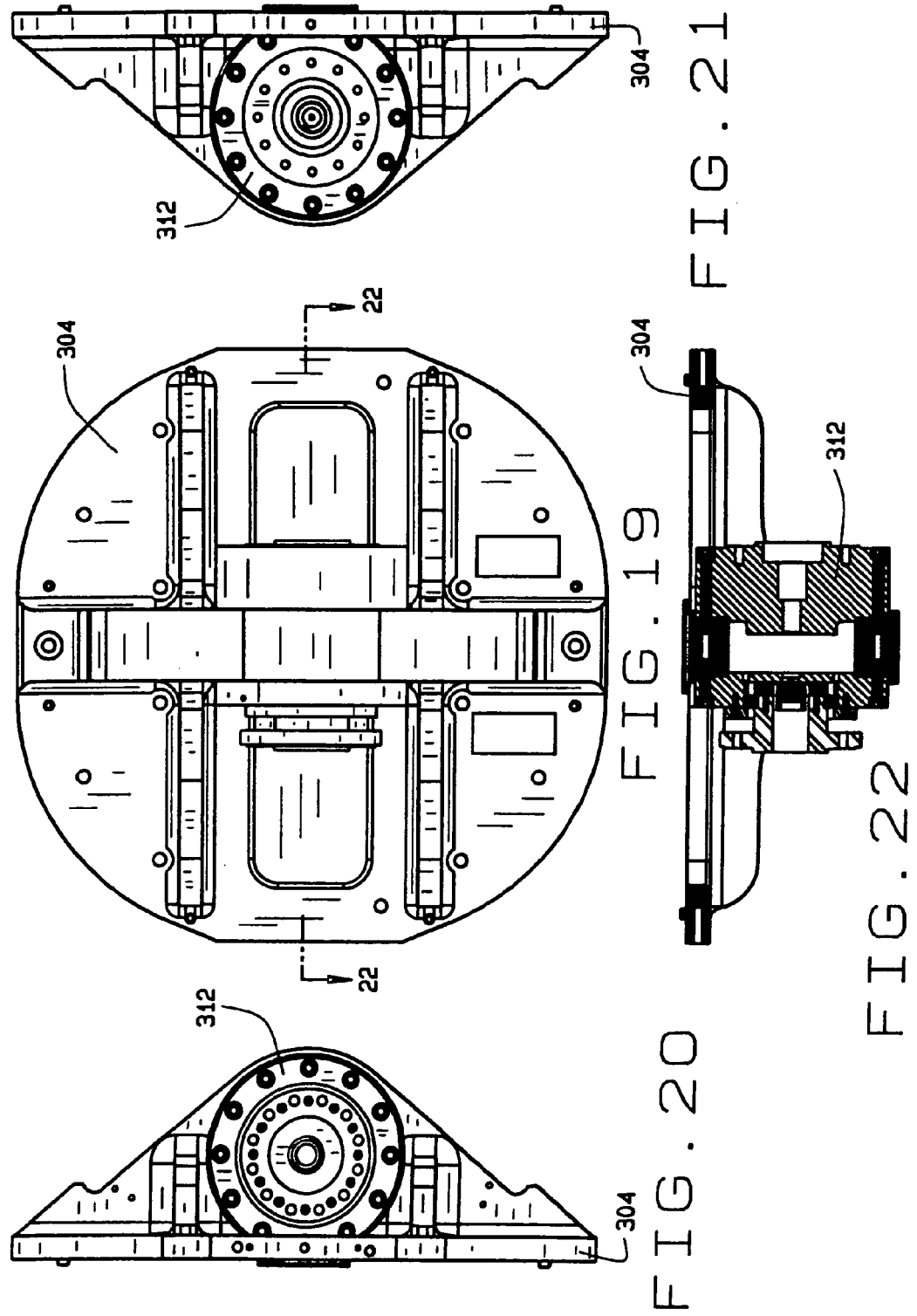

ROTATING AND PIVOTING MAGNET FOR MAGNETIC NAVIGATION

CROSS REFERENCE TO RELATED APPLICATION

This is a continuation of U.S. patent application Ser. No. 10/946,634, filed Sep. 21, 2004, now U.S. Pat. No. 7,313,429 for Method For Safely And Efficiently Navigating Magnetic Devices In The Body, which is a continuation-in-part of U.S. patent application Ser. No. 10/347,525, filed Jan. 17, 2003, now U.S. Pat. No. 7,019,610 for Magnetic Navigation System, which is a continuation-in-part of U.S. patent application Ser. No. 10/056,227, filed Jan. 23, 2002, now U.S. Pat. No. 6,975,197 for Rotating and Pivoting Magnet for Magnetic Navigation; this continuation application also claims priority to U.S. patent application Ser. No. 10/796,568, filed Mar. 9, 2004, now U.S. Pat. No. 7,264,584 which is a continuation of U.S. patent application Ser. No. 09/678,640, now U.S. Pat. No. 6,702,804, for Method For Safely And Efficiently Navigating Magnetic Devices In The Body, which claims priority to Provisional Application 60/157,619, filed Oct. 4, 1999, now abandoned; all of the above applications are incorporated herein by reference.

BACKGROUND OF THE INVENTION

This system relates to magnetic navigation of medical devices in the body, and in particular to a system for applying a magnetic field of selected direction to an operating region in a subject's body to orient a magnetically responsive medical device.

Magnetic navigation of medical devices has significantly improved to ability of medical professionals to control medical devices in the body. Early magnetic navigation techniques involved the use of superconducting magnets. While these techniques were, and remain, highly effective, advances in permanent magnetic materials and in the design of permanent magnets, have made it possible to use permanent magnets for magnetic navigation. While the magnetic fields created by superconducting magnets can be readily changed by changing the currents in the superconducting electromagnetic coils, in order to change the magnetic field created by permanent magnets for navigation, it is generally necessary to change the position and/or orientation of the permanent magnet. In order to accurately control the magnetic field applied by permanent magnets, it is necessary to accurately control the position and/or orientation of the permanent magnet.

SUMMARY OF THE INVENTION

The present invention relates to a magnetic navigation system, and in particular to a system including magnet units comprising a permanent magnet, and a support for controlling the position and orientation of a permanent magnet. The system is adapted for magnetically navigating a medical device in an operating region within the body of a patient. Generally, the system comprises a magnet having a front field projecting from the front of the magnet sufficient to project a magnetic field into the operating region in the patient. The magnet is mounted for movement between a navigation position in which the magnet is located adjacent to the patient with the front of the magnet generally facing the operating region, and an imaging position in which the magnet is spaced from the patient and the front generally faces away from the operating region.

According to another aspect of the invention, the system includes a magnet system comprising: a magnet and a support for mounting the magnet and changing the position and orientation of the magnet to change the direction of magnetic field applied to the operating region. The support is preferably capable of pivoting the magnet about a first axis that rotates about a second axis perpendicular to the first axis, and translating the magnet, preferably parallel to the second axis.

In a second embodiment the support preferably also provides for rotation of the magnet around the operating region, to accommodate rotation of an imaging system about the operating region.

BRIEF DESCRIPTION OF THE DRAWINGS

FIG. 19 is a front elevation view of the front plate of the phi drive mechanism;

FIG. 20 is a left side elevation view of the front plate of the phi drive mechanism;

FIG. 21 is a right side elevation view of the front plate of the phi drive mechanism;

FIG. 22 is a horizontal transverse view of the front plate of the phi drive mechanism, taken along the plane of line 22-22 in FIG. 19;

Corresponding reference numerals indicate corresponding parts throughout the several views of the drawings.

DETAILED DESCRIPTION OF THE INVENTION

Figure 1:
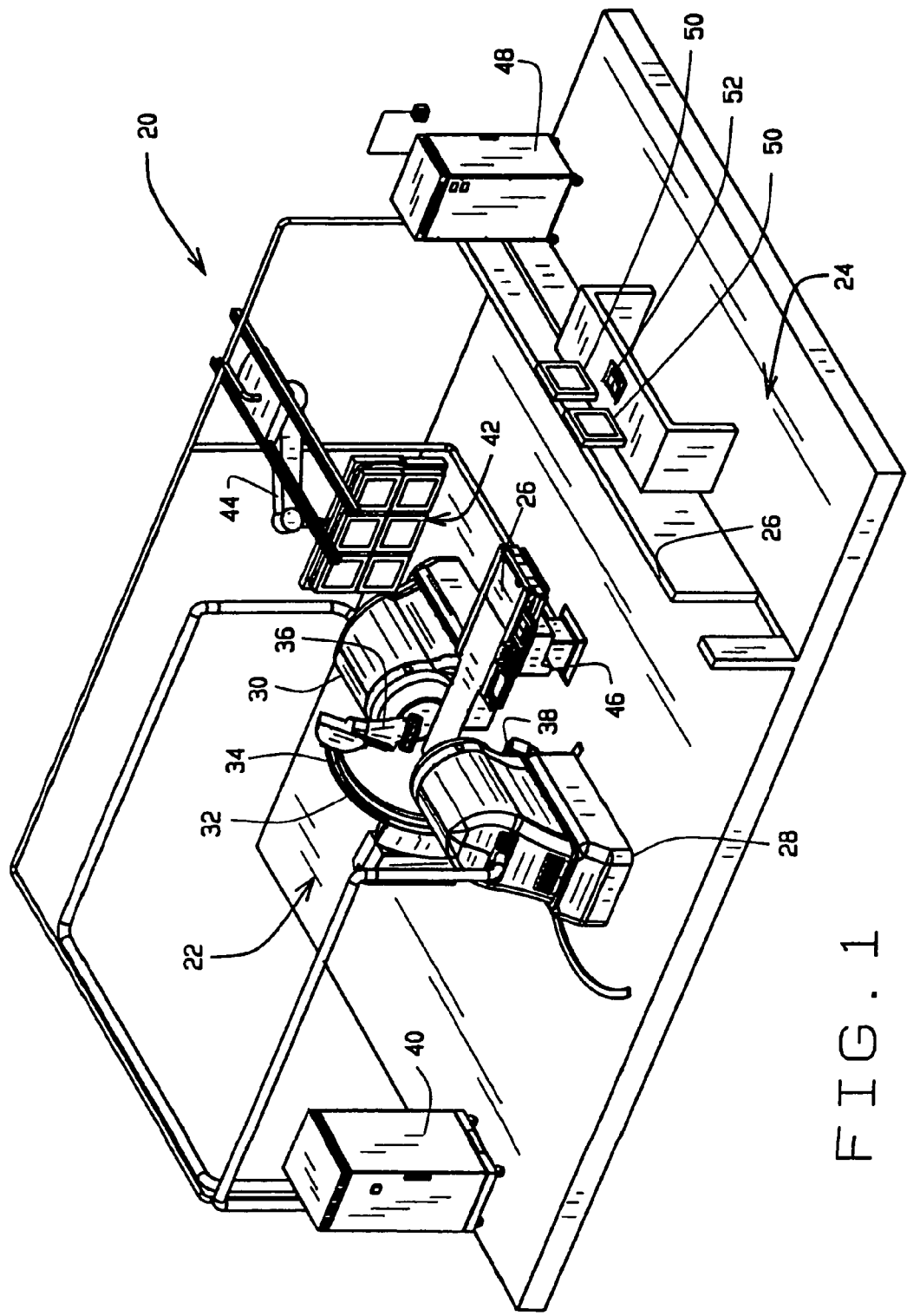
FIG. 1 is a perspective view of a magnetic surgery suite incorporating magnet assemblies in accordance with the principles of this invention.
Figure 1A:
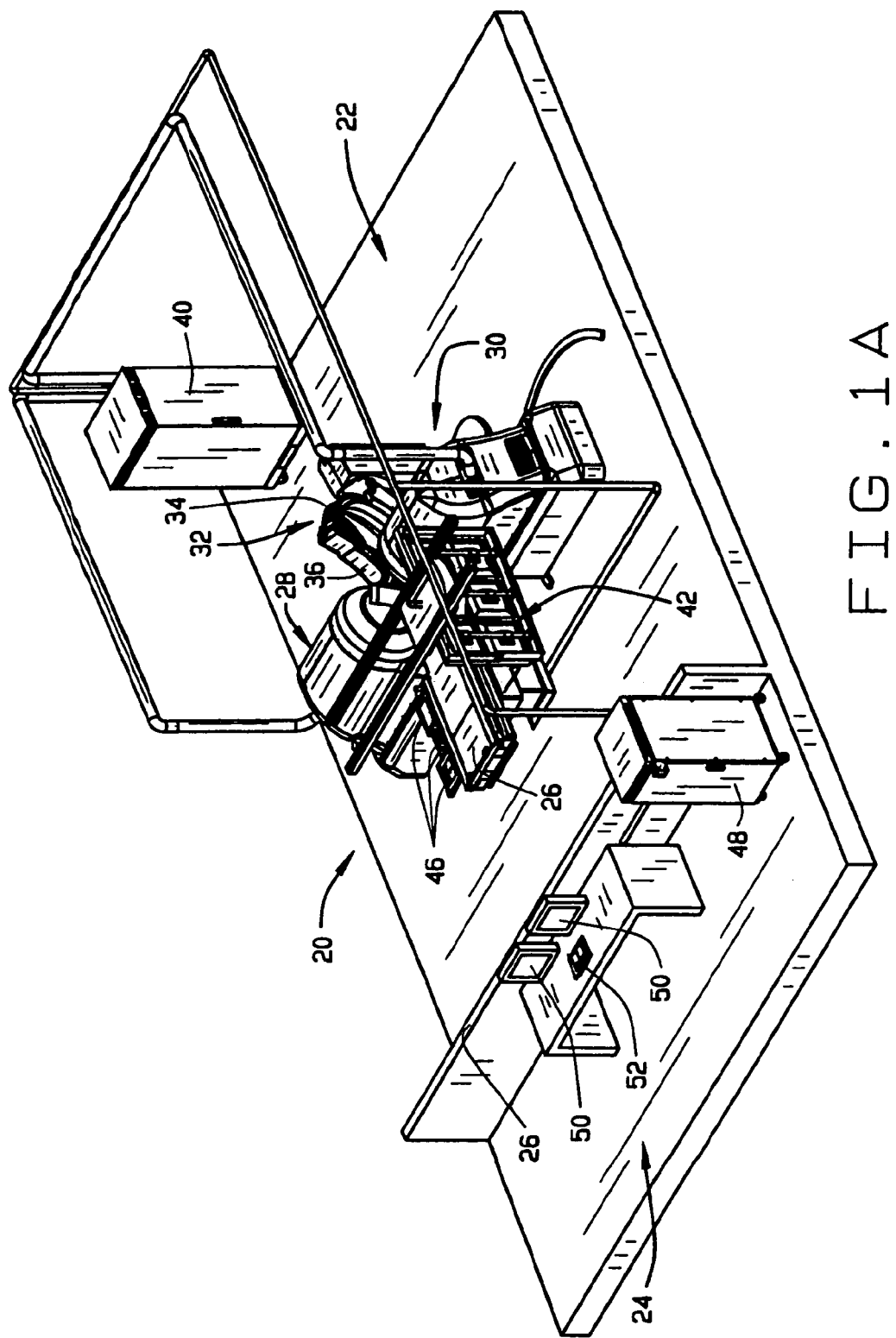
FIG. 1A is a top plan view of the magnetic surgery suite.

A magnetic surgery suite incorporating magnet units in accordance with the principles of this invention is indicated generally as 20 in FIG. 1. As shown in FIG. 1, the suite 20 comprises an operating room 22 and a control room 24. The control room 24 is preferably adjacent to the operating room 22, and has a window 26 from which the procedure taking place in the operating room 22 can be viewed. However, the control room 24 does not have to be adjacent to the operating room 22, and instead could be located remotely from the operating room, for example on a different floor, or in a different building, or even in a different city.

The operating room 22 includes a patient support, such as a patient bed 26, and a pair of magnet units 28 and 30, disposed on opposite sides of the patient bed to project a magnetic field into the operating region in a patient on the patient bed. The operating room also includes an imaging system 32, comprising a C-arm mounting at least one x-ray source 34 and at least one x-ray receiver 36, such as an amorphous silicon imaging plate. Cabinets 38 and 40 are provided for computer controllers and other electronics for operating the magnet units 28 and 30 and the imaging system 32. A plurality of displays 42 (six in this preferred embodiment) are mounted on an articulating arm 44 from the ceiling. The displays 42 display images from the imaging system 32, and screens from the control system for operating the magnet units 28 and 30. A plurality of controls 46 are provided on the patient bed 26 for operating a user interface to control the magnet units 28 and 30, in conjunction with the screens displayed on the displays 42.

The control room 24 includes a cabinet 48 for a processor for operating the user interface for controlling the magnet units 28 and 30. A plurality of displays 50 (two in this preferred embodiment) are provided for displaying images from the imaging system 32, and screens from the user interface. A plurality of controls 52 are provided on the patient bed 26 for operating a user interface to control the magnet units 28 and 30, in conjunction with the screens on the displays 52.

Each of the magnet units 28 and 30 projects a strong magnet field from its front face, so that together, the magnets provide a magnet field of sufficient strength to orient a magnetic medical device in an operating region in the patient on the patient bed 26. Because of the strength of the field projected by the magnet units 28 and 30, the units are preferably rotatably mounted to swing between an operative position in which the units face the patient support, and project a field into the operating region in the patient on the patient bed, and a stowed position, in which the magnet units do not face the patient bed.

Figure 2:
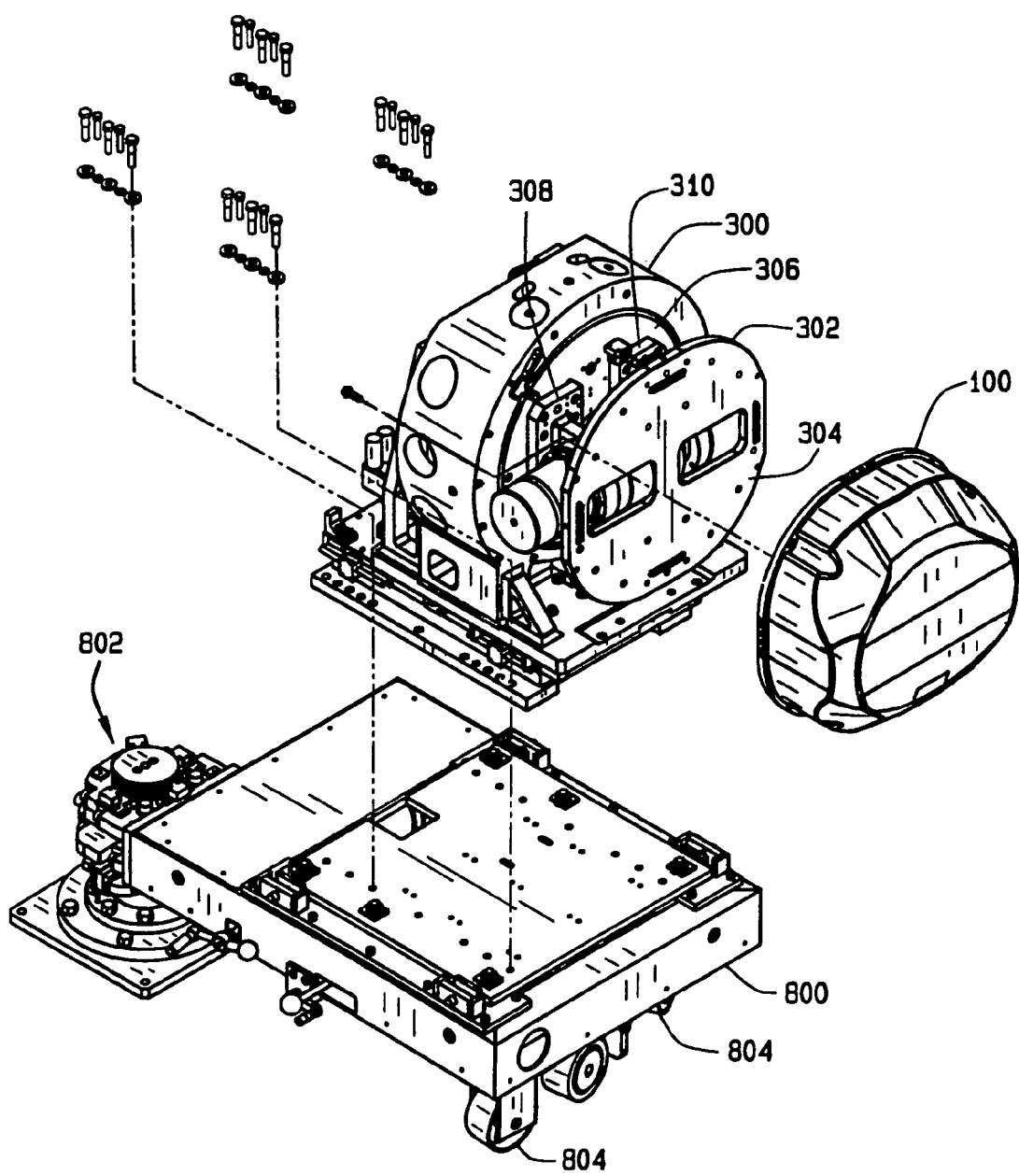
FIG. 2 is an exploded front perspective view of one of the magnet assemblies (the other magnet assembly being a mirror image thereof), with the cover removed to show details of construction.

As shown in FIG. 2, each of the magnet units 28 and 30 comprises a magnet 100, a mechanism 200 for moving the magnet to change the magnetic field applied by the magnet 100 to the operating region in a patient, and a pedestal 700, for supporting the mechanism 200 and magnet 100. As described in more detail below the magnet 100 is preferably a compound magnet designed so that relatively small translations and/or rotations result in significant changes in the magnetic field direction projected into an operating region in the patient. As described in more detail below, the mechanism 200 is adapted to support and translate and/or rotate the magnet 100 to change the direction of the field applied by the magnet to the operating region in the patient. The magnet 100 and the mechanism 300 are preferably designed so that they can project a magnetic field in any direction in the operating region in the patient, or at least so that when both magnet units 28 and 30 are positioned on opposite sides of the patient, the combined effect of the magnets from the units projects a magnetic field in any direction.

In this preferred embodiment, the mechanism preferably provides three movements of the magnet 100: translation of the magnet toward and away from the patient (referred to herein as translation in the z-direction), rotation of the magnet about an axis parallel to the z-direction, referred to herein as rotation about the θ-axis, and pivoting of the magnet about an axis perpendicular to the θ-axis, referred to herein as pivoting about the φ axis. The movements of the magnet 100 in the z direction, about the θ-axis, and about the φ axis permitted by the mechanism 300 are sufficient to create a magnetic field of suitable strength for magnetic navigation, in any direction in the operating region in the patient. Of course, additional or different translations and or rotations could be provided for the same or different magnet design. The strength of the field projected by the magnets is preferably at least 0.05 Tesla, and more preferably at least 0.09 Tesla.

The magnet 100 is preferably comprised of a plurality of block 102 arranged and mounted on a backing plate 104, for example with adhesive the magnet 100 further includes a cover 106, preferably with a smooth, contoured finished surface enclosing the assembly of blocks 102. Each of the blocks is made of a permeable magnetic material, and has a size, shape, position and magnetization direction to optimize field properties (direction and strength) while accommodating manufacturing. Examples of suitable magnets are disclosed in magnets such as those disclosed in U.S. patent application Ser. No. 10/082,715, filed Feb. 25, 2002, U.S. patent application Ser. No. 10/056,227, filed Jan. 23, 2003, and/or U.S. patent application Ser. No. 09/546,840, filed Apr. 11, 2000, the disclosures of all of which are incorporated herein by reference.

The magnet 100 and mechanism 300 are mounted on pedestal 800. As indicated above, and described in more detail below, the pedestal 800 is mounted for pivoting about a post 802, and has wheels 804 which allow the pedestal to pivot from a stowed position, in which the magnet 100 generally faces away from the patient, to an operative position in which the magnet generally faces the patient.

Figure 3:
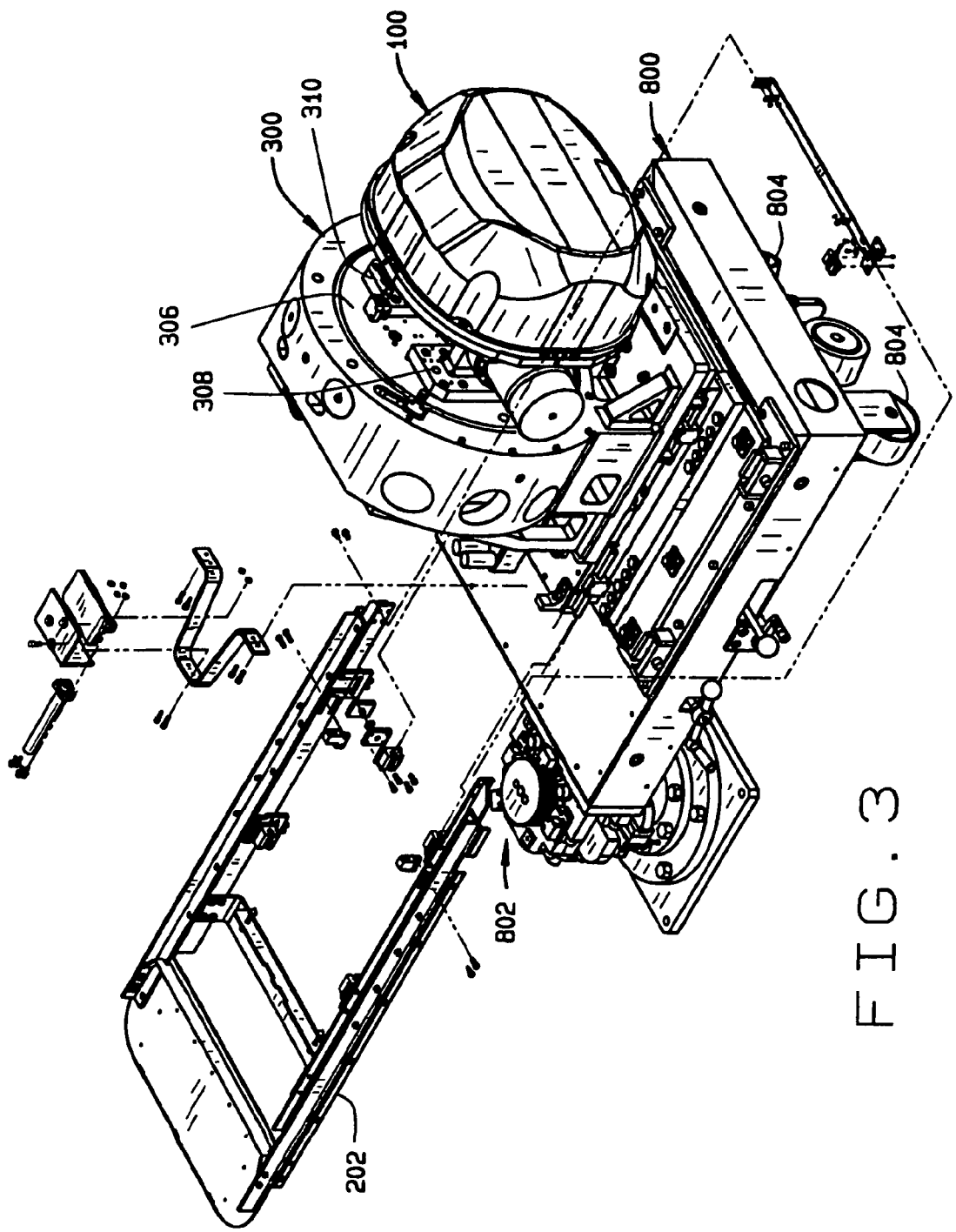
FIG. 3 is a front perspective view of the magnet assembly, with the cover removed.
Figure 4:
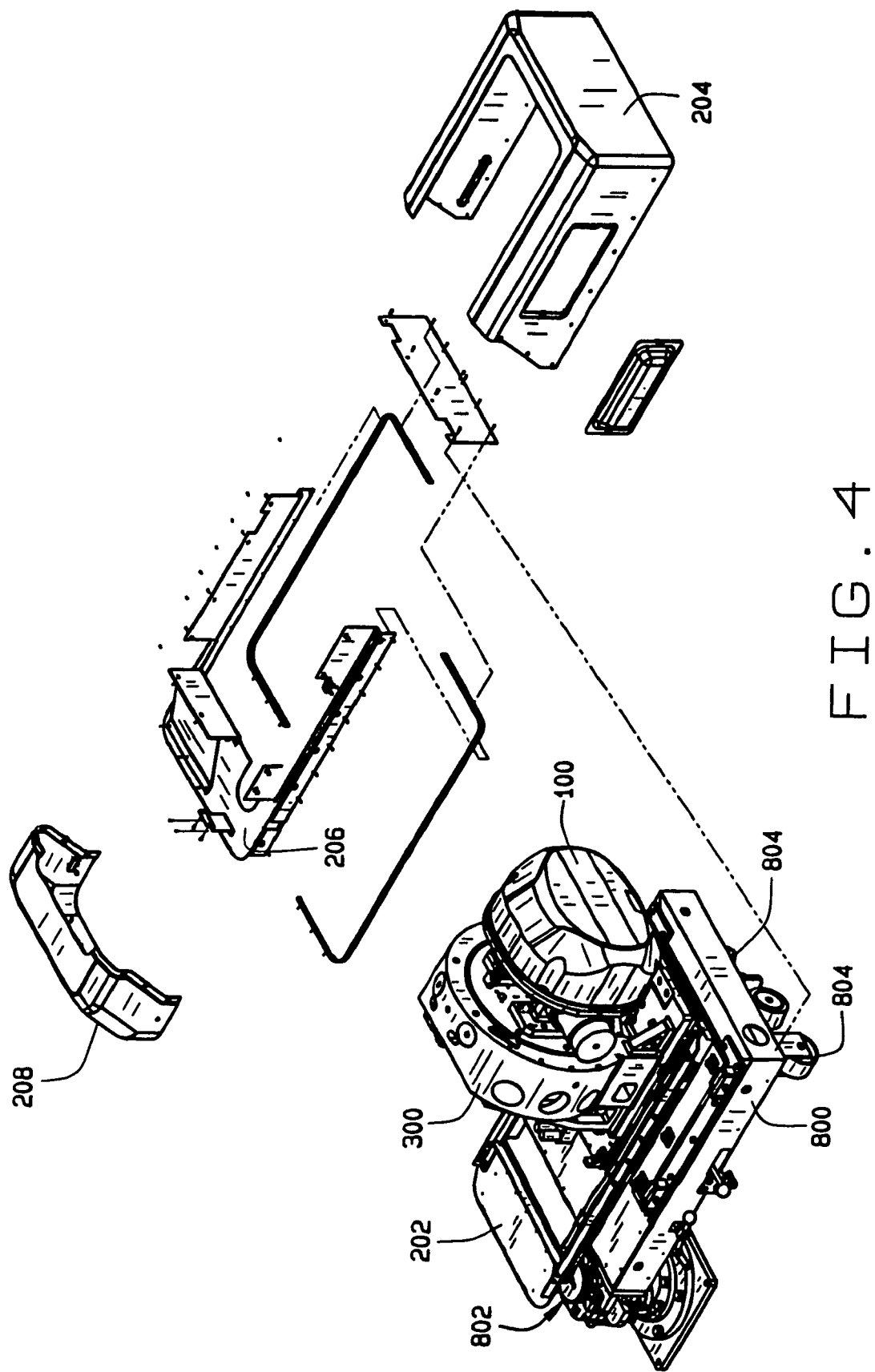
FIG. 4 is a front perspective view of the magnet assembly, showing the lower cover.
Figure 5:
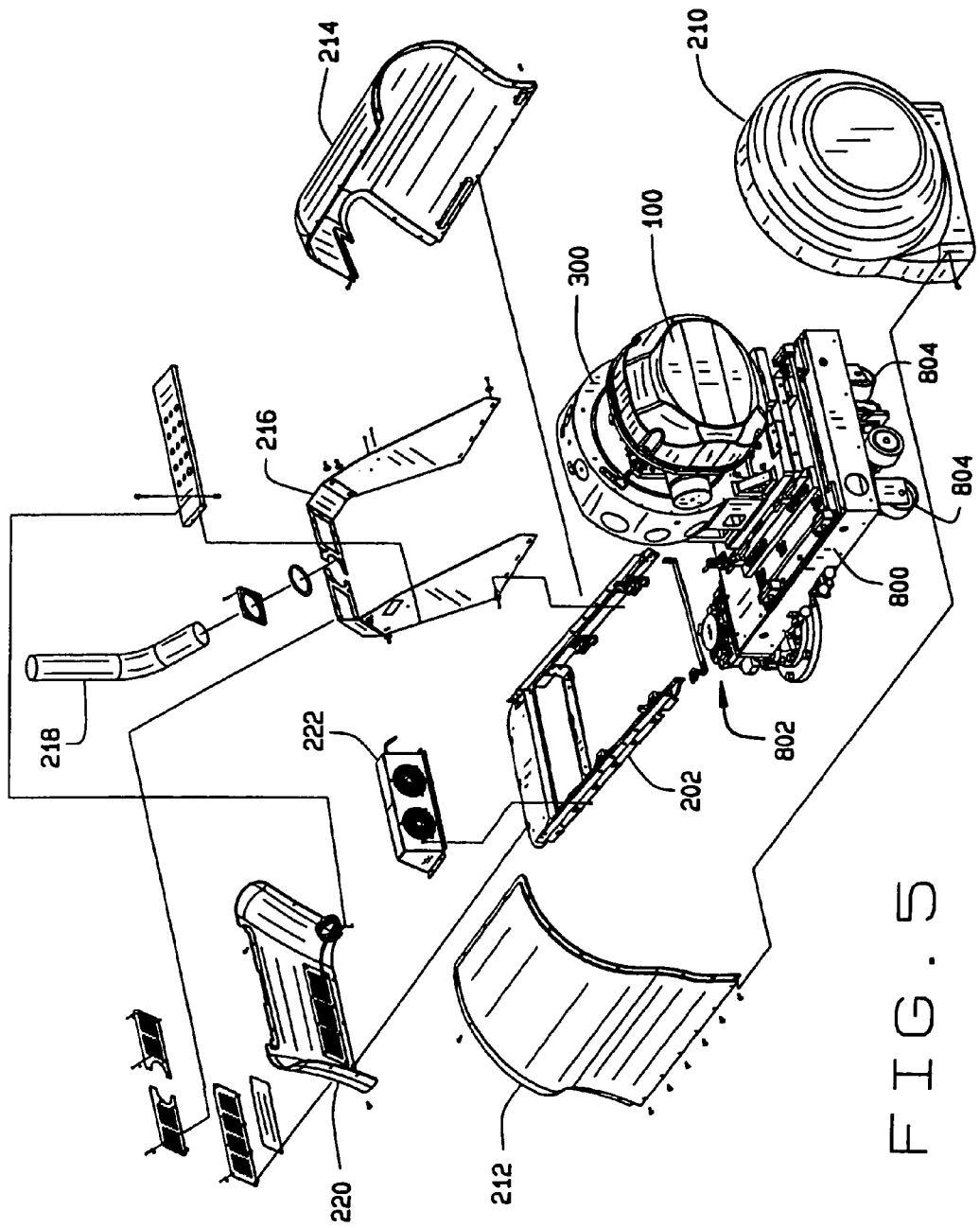
FIG. 5 is a front perspective view of the magnet assembly, showing the upper cover.
Figure 6:
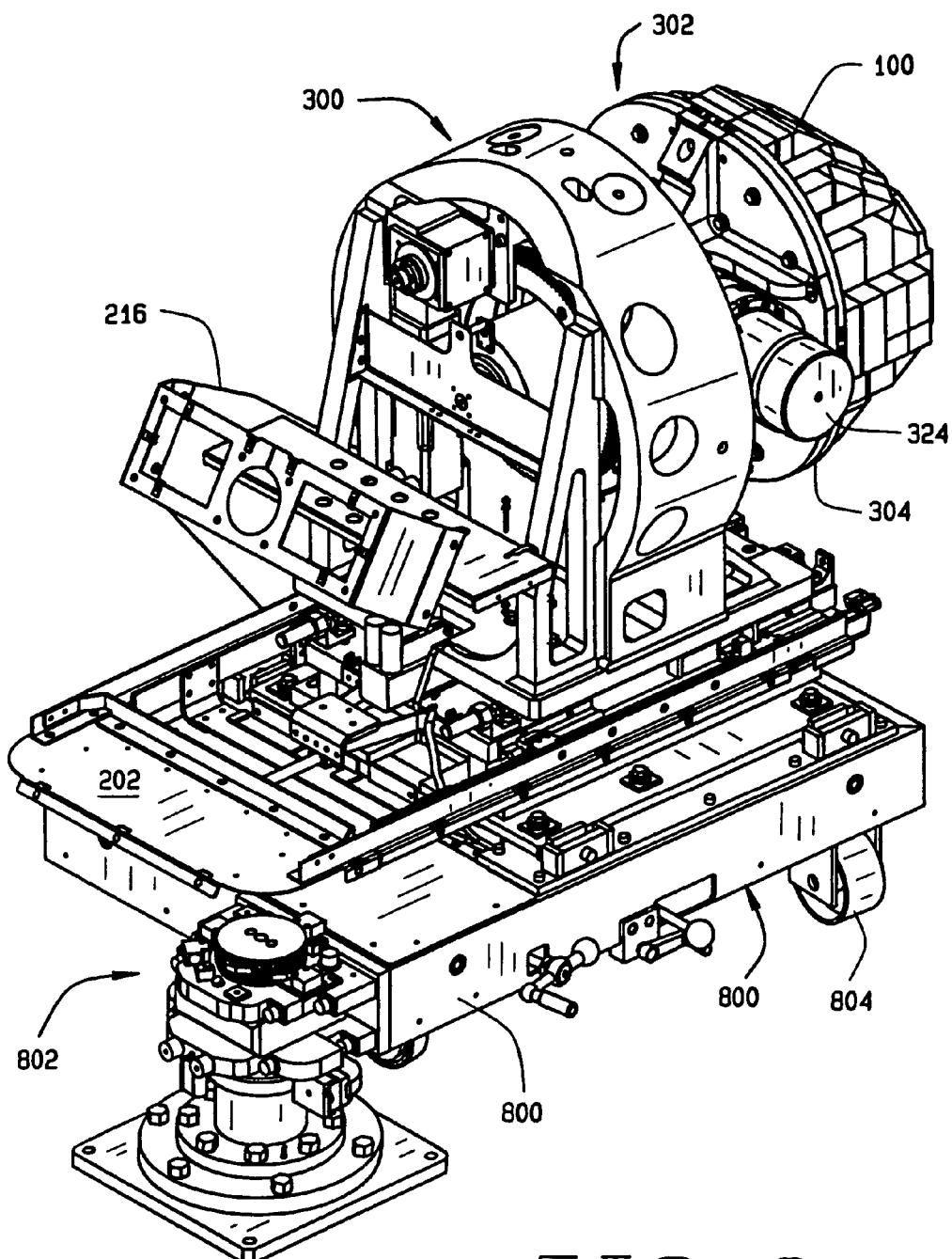
FIG. 6 is a rear perspective view of the magnet assembly.
Figure 7:
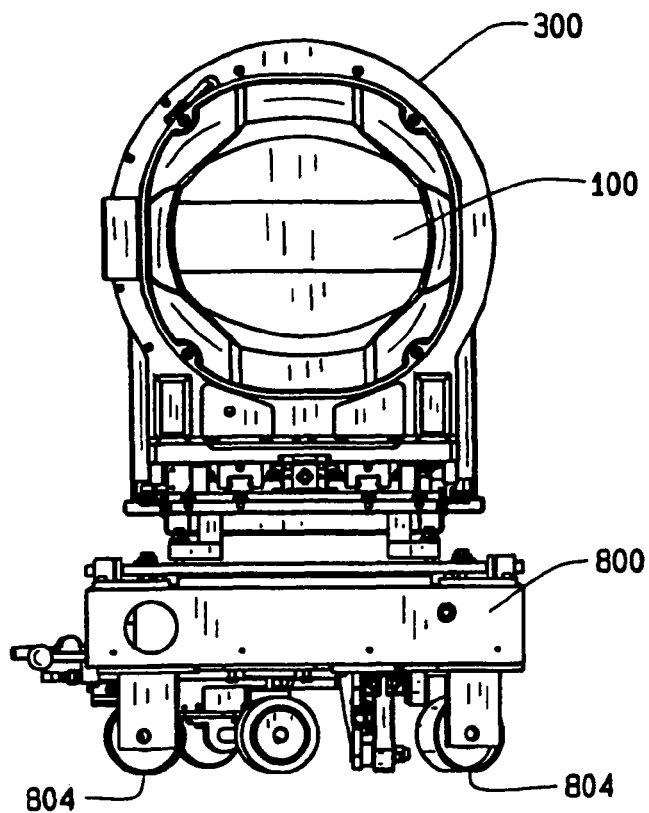
FIG. 7 is a front elevation view of the magnet assembly.
Figure 9:
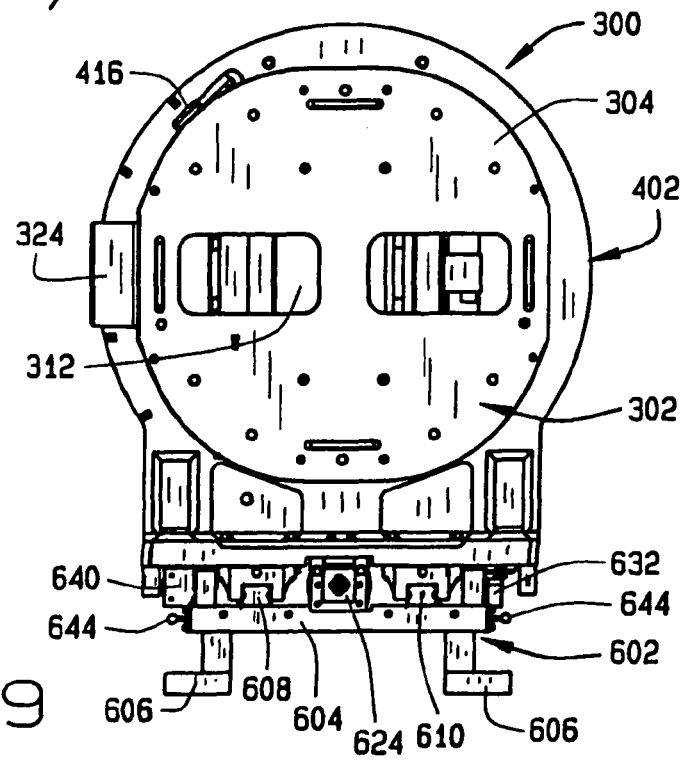
FIG. 9 is a front elevation view of the positioner system of the magnet assembly.

The magnet 100 and mechanism 300 are preferably enclosed is a cover 200 to protect the mechanism from interference, to prevent persons from being injured or property from being damaged by the mechanism, to reduce patient anxiety, and to enhance the appearance of the unit. As shown in FIG. 3, this cover includes a frame 202 slidably mounted around the base of the mechanism 300. As shown in FIG. 4, the cover also comprises a front base cap 204, which is generally U-shaped and adapted to be secured on the front and sides of the pedestal 800, a top base cap 206, which is adapted to be secured over the top of the pedestal, around the mechanism 300, and a rear base cap 208, which is adapted to be secured on the back of the pedestal cap device. As shown in FIG. 5, the cover 200 also comprises a front panel 210, adapted for mounting on the frame 202 over the front of the magnet 100 and mechanism 300, and left and right side panels 212 and 214 adapted for mounting on the frame 202 over the sides of the magnet and mechanism. An inverted U-shaped frame 216 is mounted on the frame 202 over the back of the mechanism 300. The frame 216 mounts a conduit 218 for enclosing power and control leads, and a back panel 220 for covering the back of the mechanism. A cooling fan unit 222 is mounted on the frame 202, inside the panel 220 to circulate air inside the cover through louvered openings formed in the cover 220.

Figure 8:
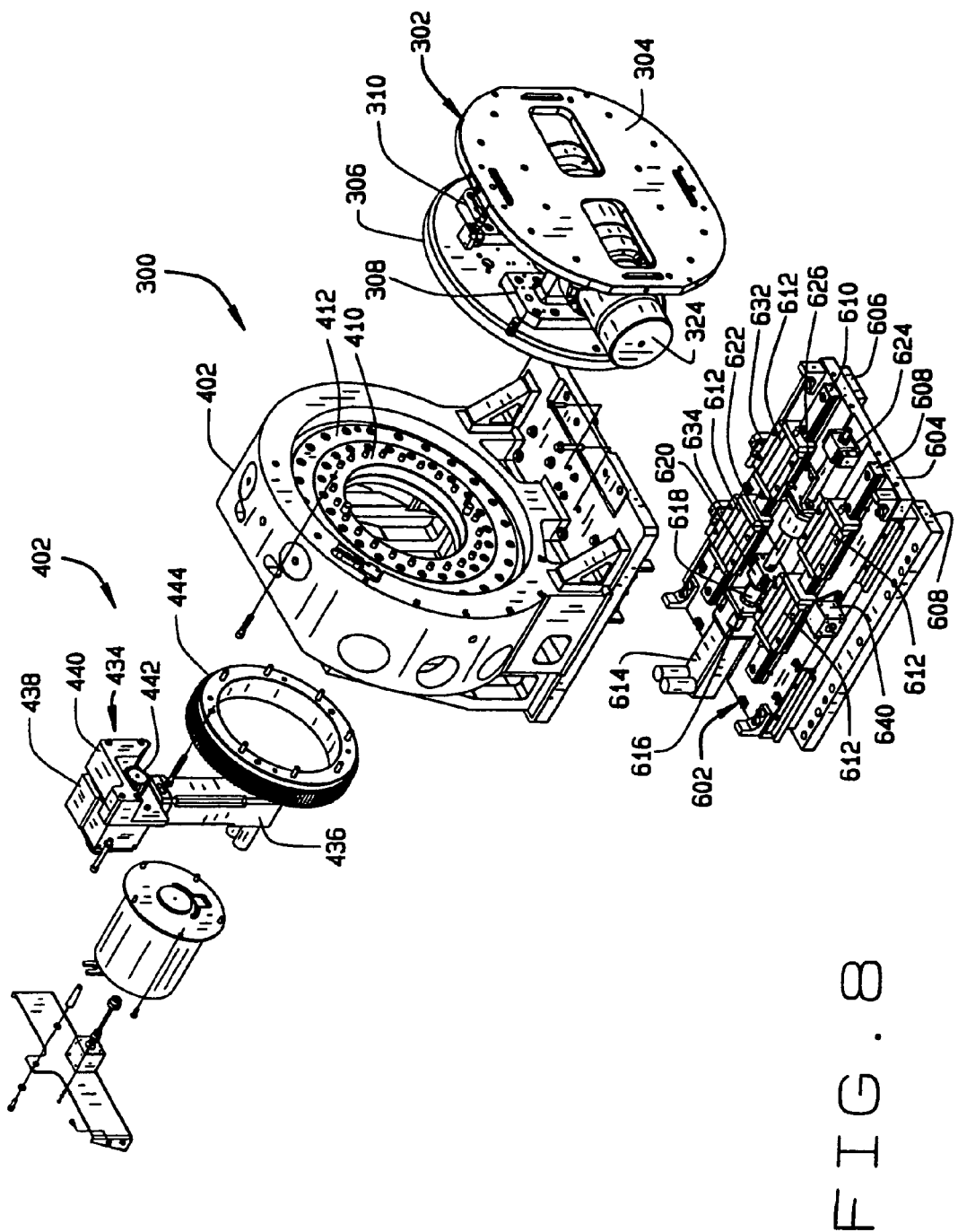
FIG. 8 is a further exploded front perspective view of the positioner system of the magnet assembly
Figure 10:
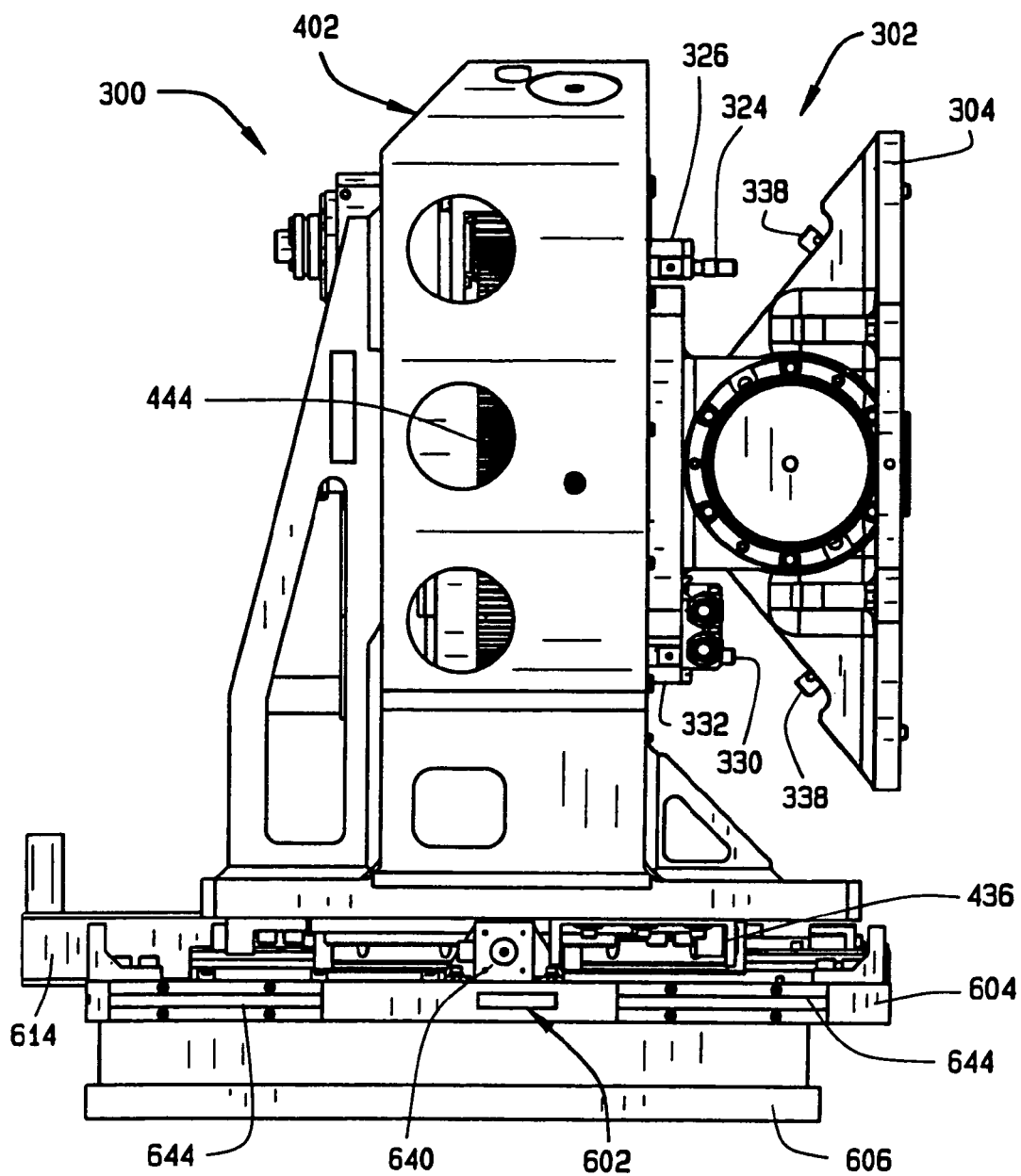
FIG. 10 is a left side elevation view of the positioner system of the magnet assembly
Figure 11:
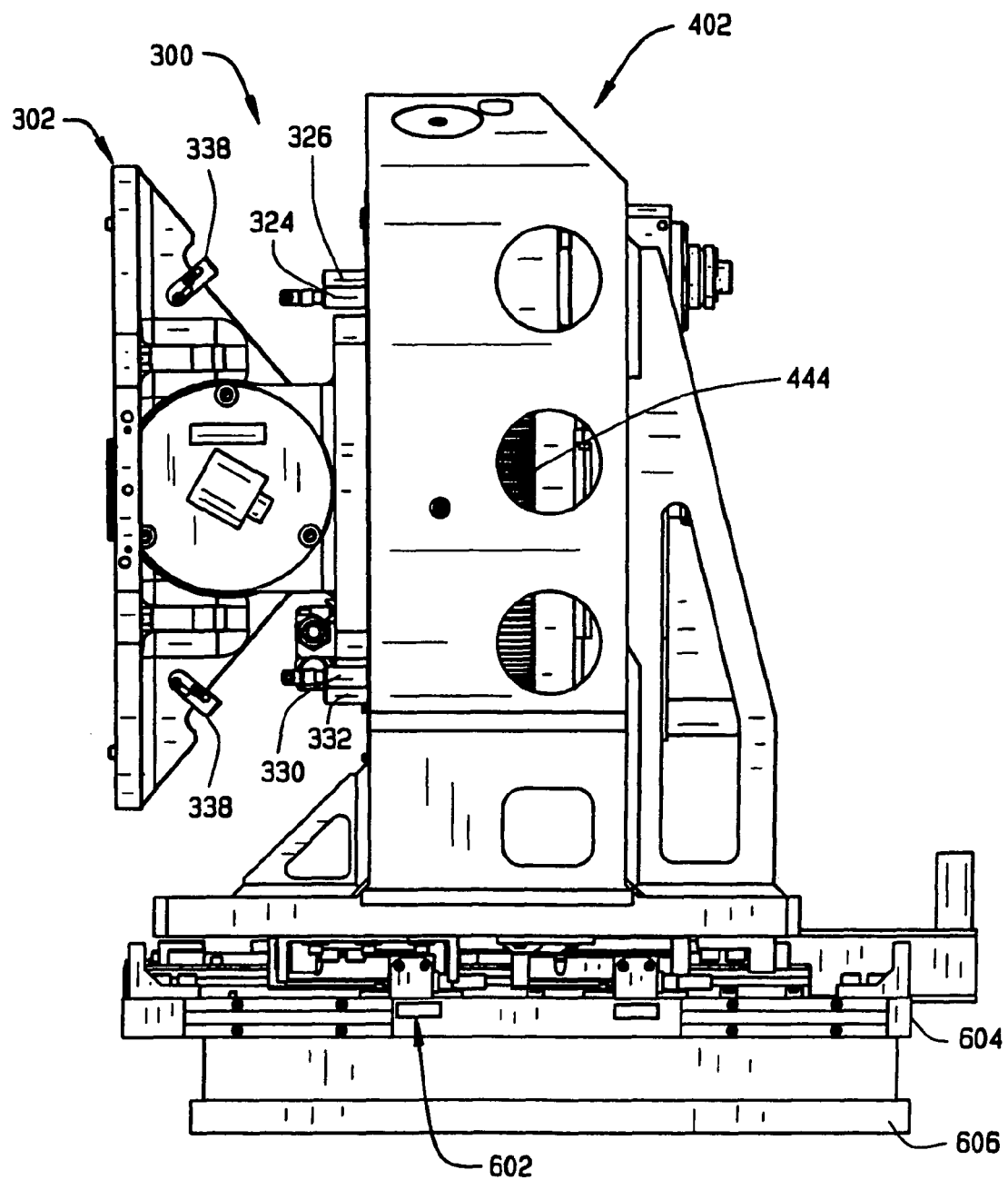
FIG. 11 is a right side elevation view of the positioner system of the magnet assembly.
Figure 12:
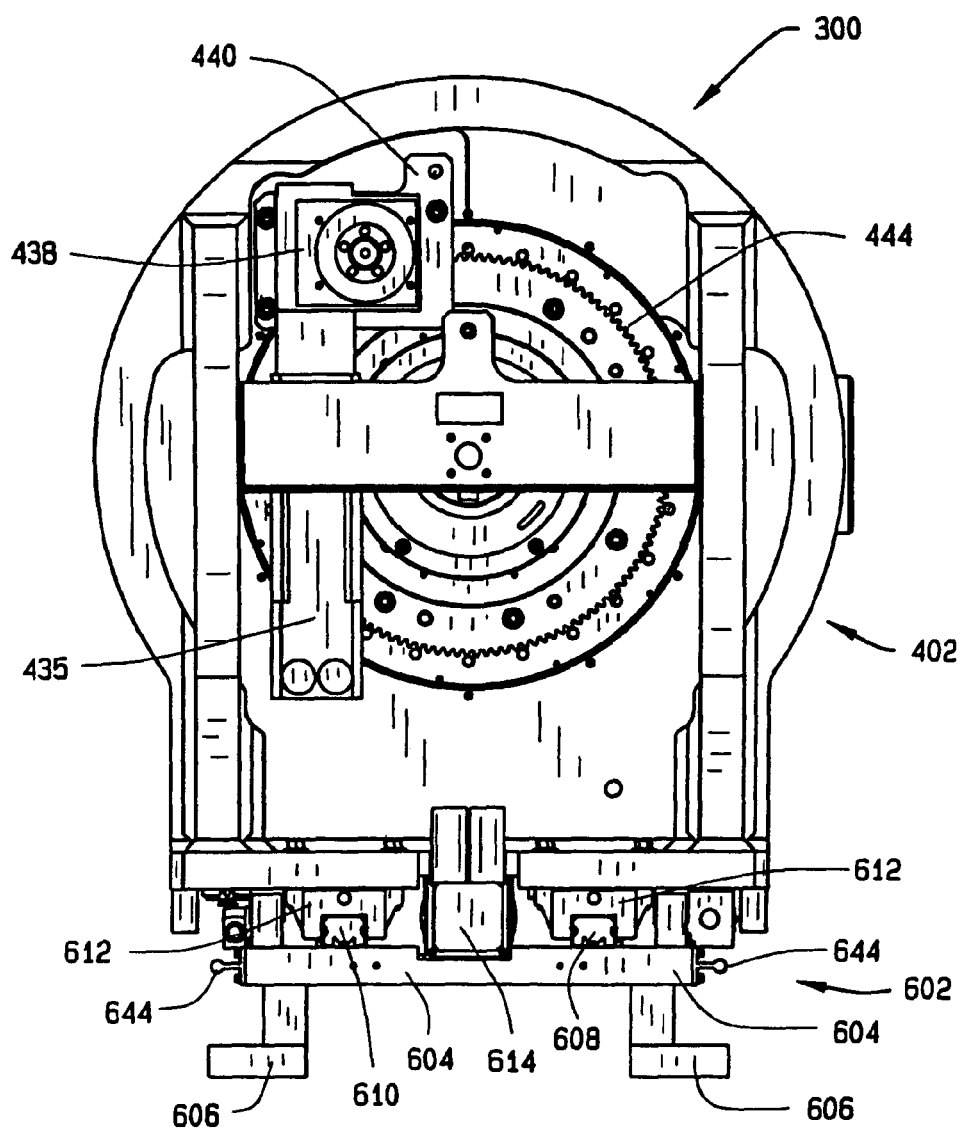
FIG. 12 is a rear elevation view of the positioner system.
Figure 13:
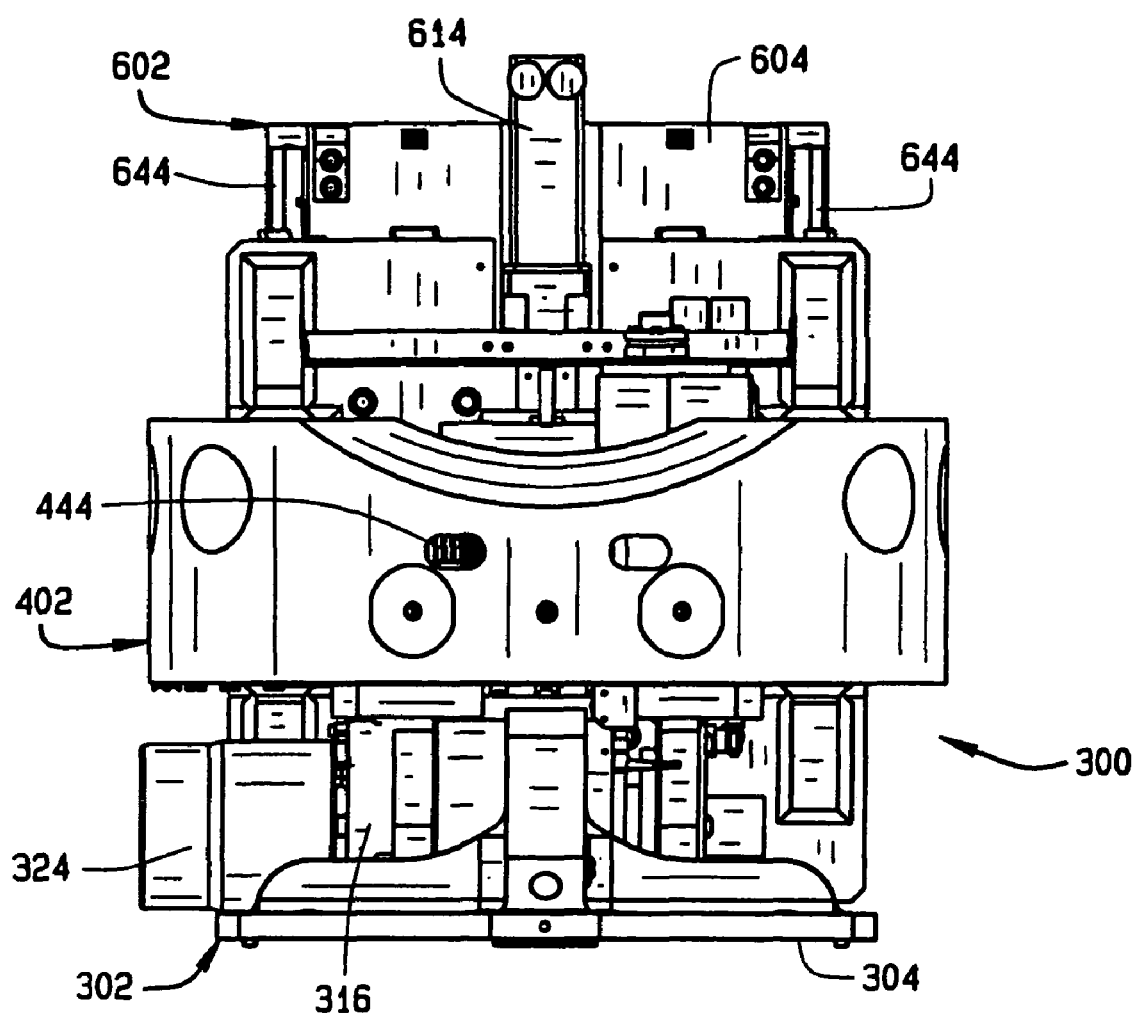
FIG. 13 is a top plan view of the positioner system.
Figure 14:
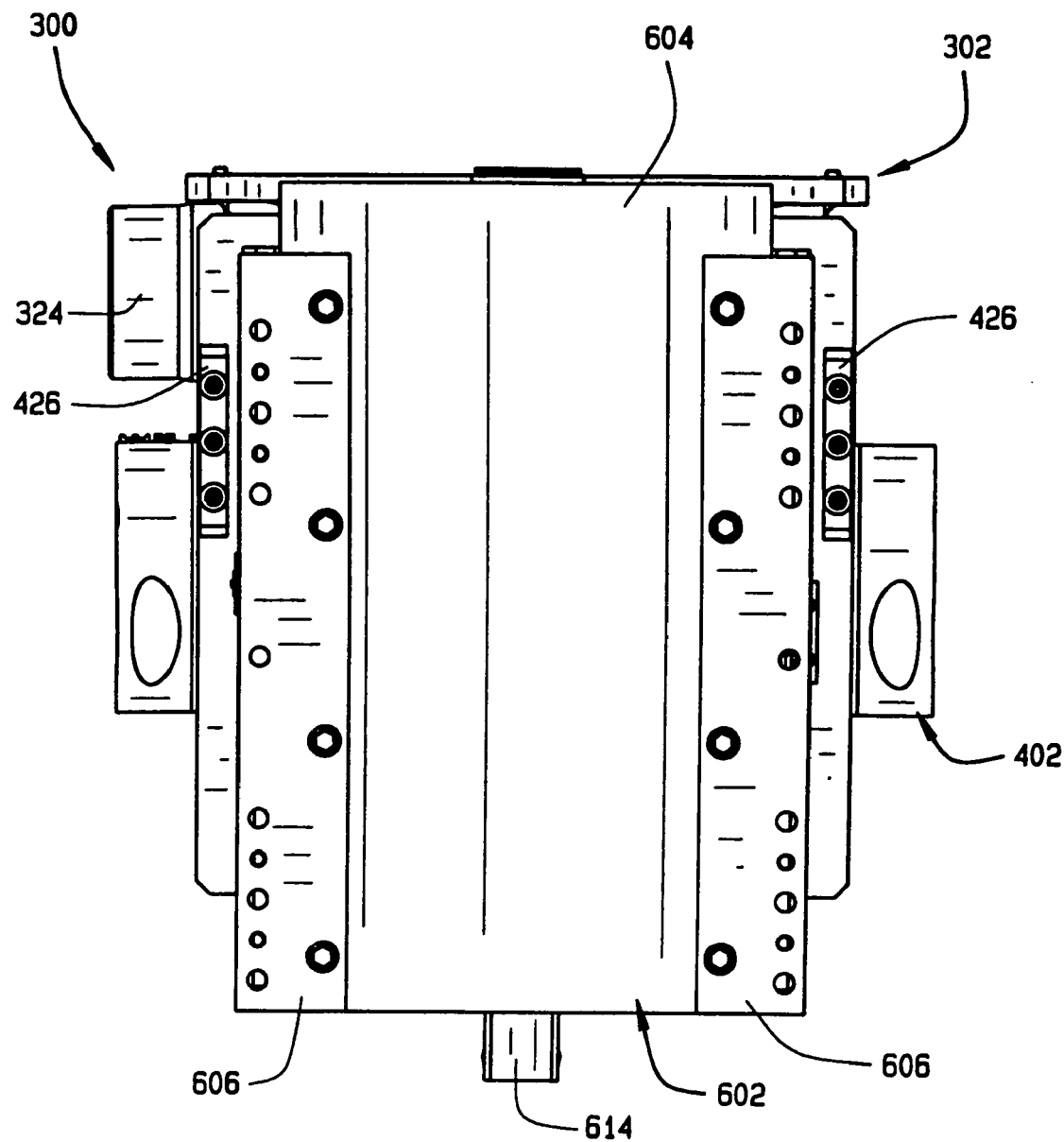
FIG. 14 is a bottom plan view of the positioner system.
Figure 15:
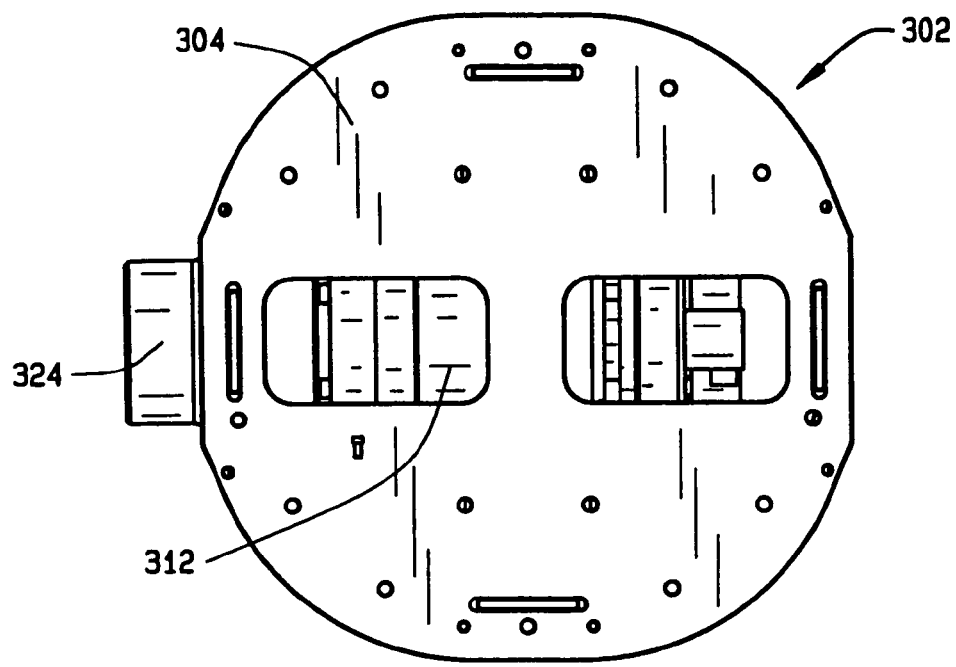
FIG. 15 is a front elevation view of the phi drive mechanism of the magnet assembly.
Figure 16:
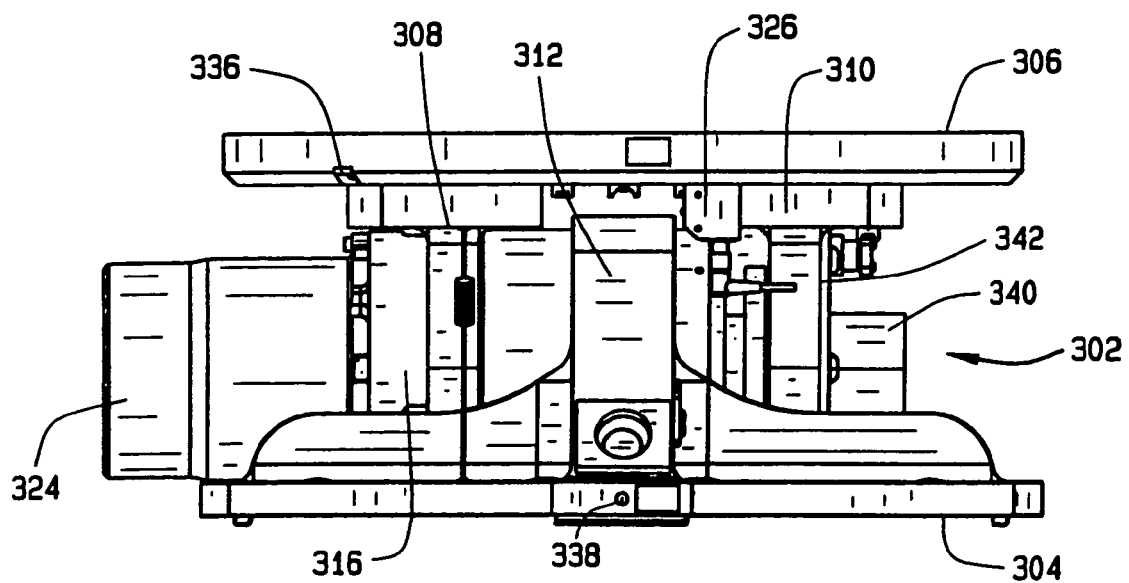
FIG. 16 is a top plan view of the phi drive mechanism.
Figure 17:
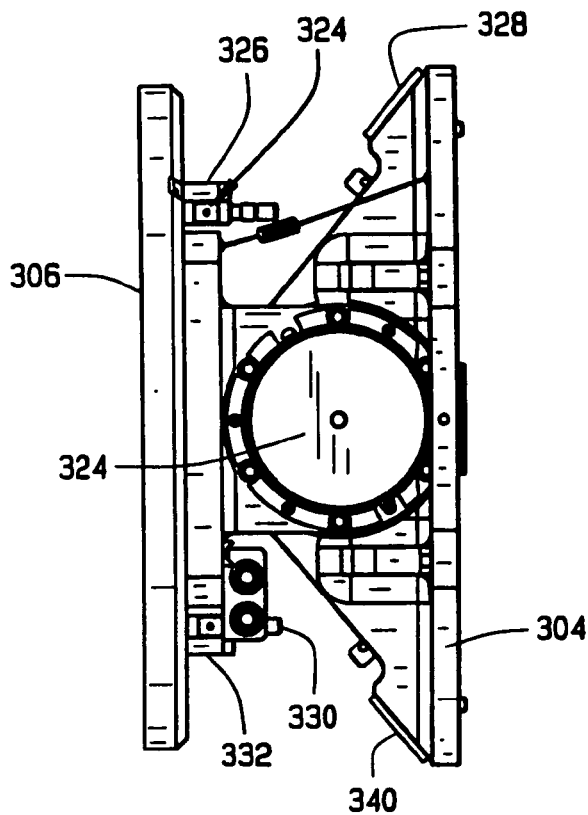
FIG. 17 is a left side elevation view of the phi drive mechanism.
Figure 18:
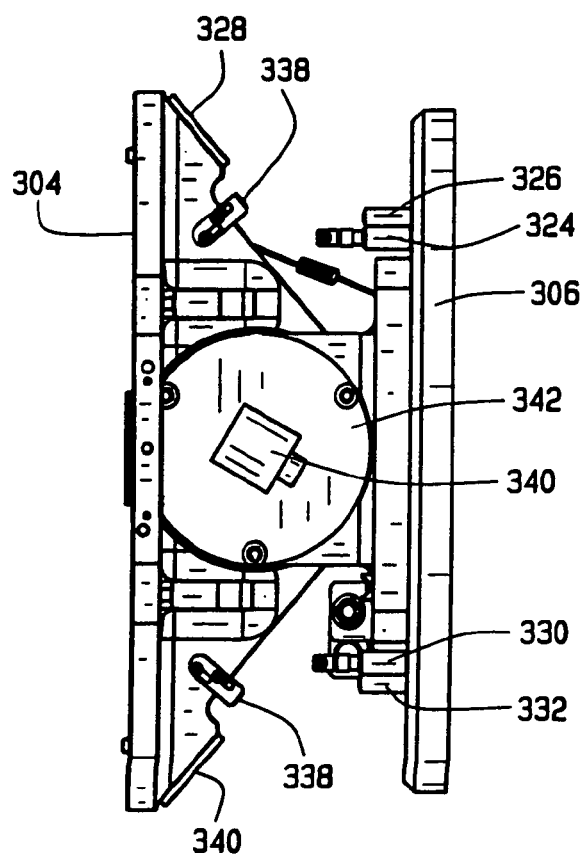
FIG. 18 is a right side elevation view of the phi drive mechanism.

As shown in FIG. 8, the mechanism 300 preferably comprises a $\phi$ pivot mechanism 302, for pivoting the magnet 100 about the $\phi$ axis; a $\theta$-rotation mechanism 402, for rotating the magnet 100 about the $\theta$-axis; and a z-drive mechanism 602 for translating the magnet in the z-direction.

As shown in FIGS. 15-22, the $\phi$ pivot mechanism 302 comprises a front plate 304, adapted for mounting the magnet 100. The front plate 304 is pivotally mounted to a back plate 306. The back plate 306 is adapted to be mounted on the $\theta$-rotation mechanism 402, and has two parallel brackets 308 and 310 projecting from its front face for mounting the front plate 304. A hub 312 on the back of the front plate 304 is pivotally mounted between the brackets 308 and 310, so that the front plate can pivot. In this preferred embodiment, the front plate 304, and thus the magnet 100 mounted on the front plate can pivot plus and minus 40°, for a total range of motion of 80°. This range of motion is based upon the properties of the magnet 100, which in this preferred embodiment provides a 180° change in field direction over a range of pivoting of 80°. With a different magnet, the range of pivoting could be made larger or smaller, as desired.

Figure 23:
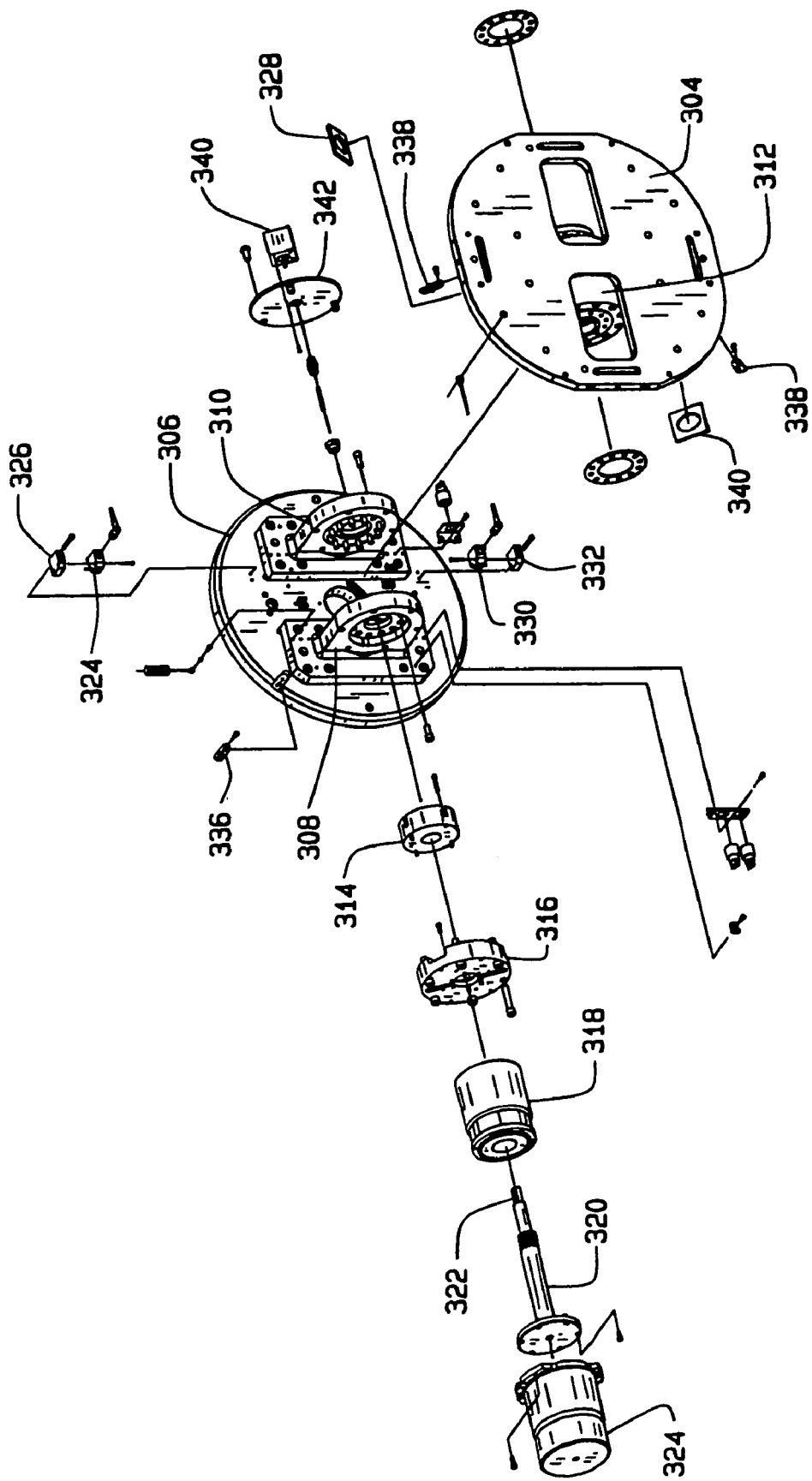
FIG. 23 is an exploded perspective view of the phi drive mechanism.
Figure 24:
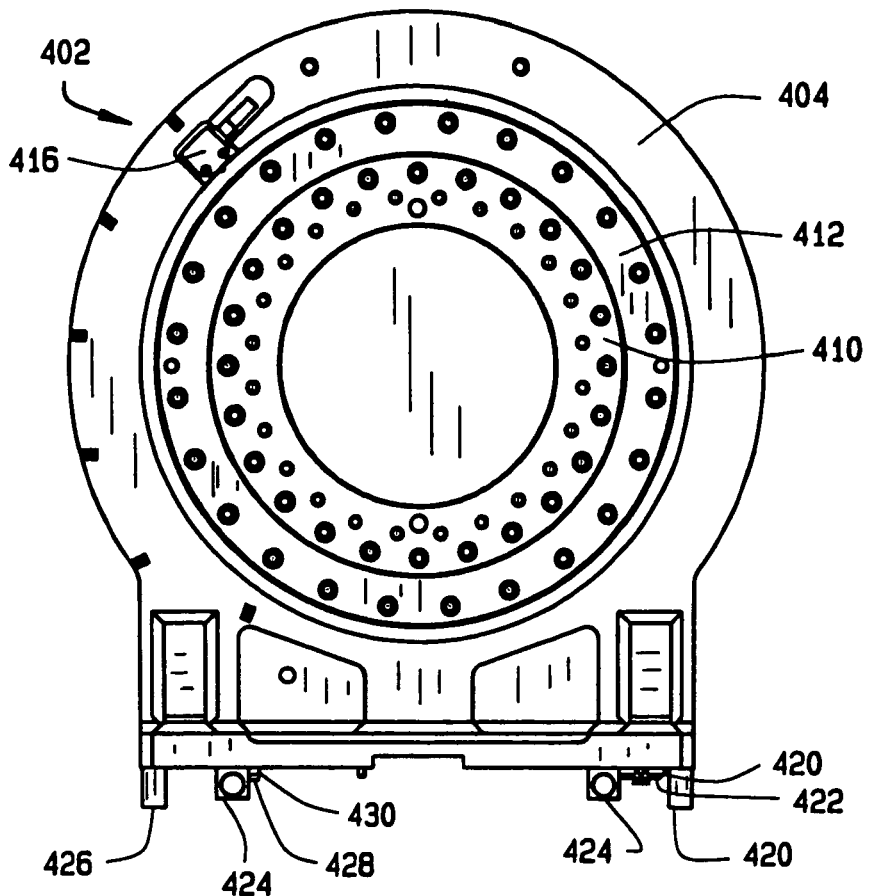
FIG. 24 is a front elevation view of the theta drive mechanism of the magnet assembly.
Figure 25:
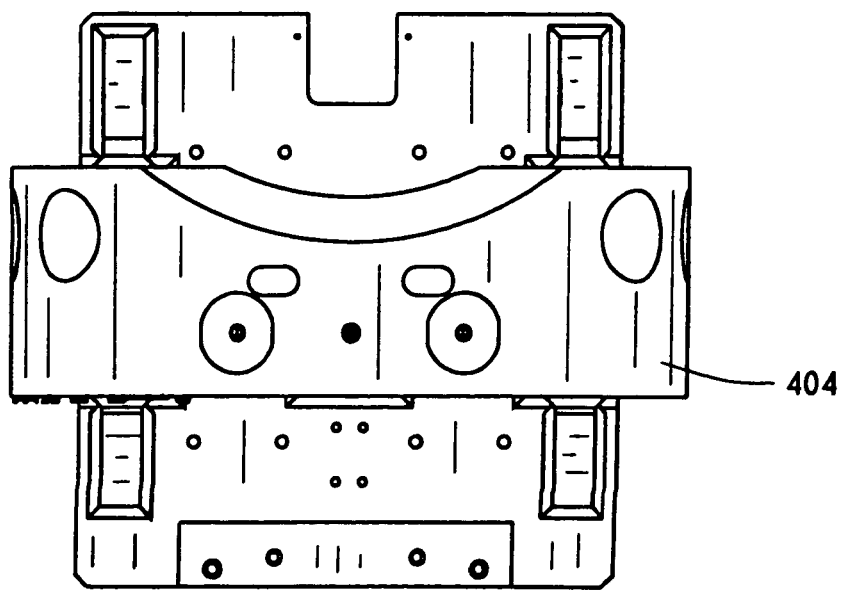
FIG. 25 is a top plan view of the theta drive mechanism.
Figure 26:
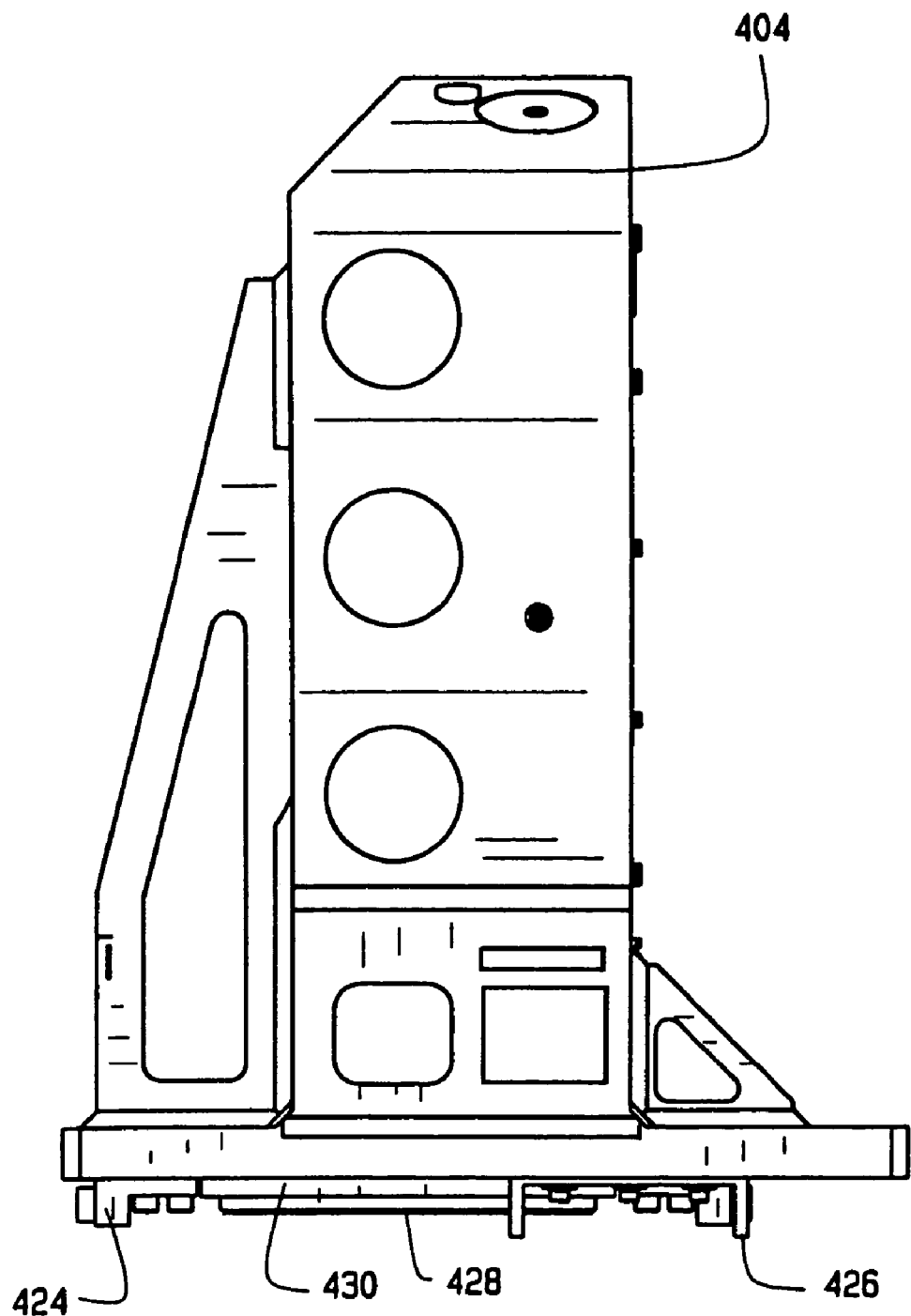
FIG. 26 is a left side elevation view of the theta drive mechanism.
Figure 27:
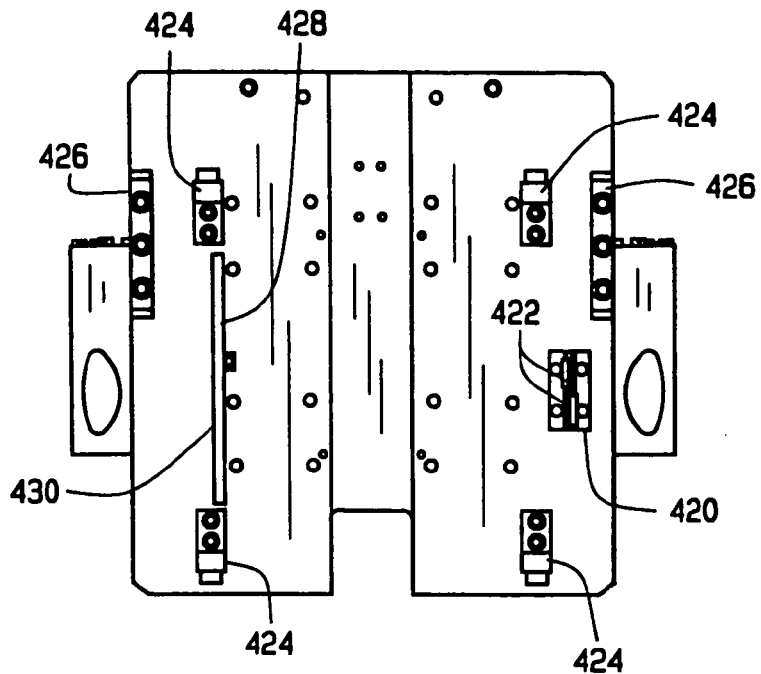
FIG. 27 is a bottom plan view of the theta drive mechanism.

As best shown in FIG. 23, a motor brake 314 is mounted on bracket 308, a motor mounting adapter 316 is mounted over the motor brake on the bracket 308. A motor 318 is mounted on the mounting adapter 316, to turn drive shaft 320 having key 322 thereon. A housing 24 encloses the motor 318. The drive shaft 320 engages the front plate 304 so that rotation of the drive shaft caused by motor 318 causes the plate to pivot about the $\phi$ pivot mechanism.

A $+\phi$ limit switch 324 is mounted on a block 326 on the front face of plate 306, and is adapted to engage a stop 328 on the front plane 304. Similarly, a $-\phi$ limit switch 330 is mounted on a block 332 on the front face of plate 308, and is adapted to engage a stop 334 on the front plate. A theta sensor flag 336, which is used by the theta position sensor as described below, is secured on the back plate 306. Phi sensor flags 338 are secured on the back of front plate 304. A rotary encoder 340 is mounted on an encoder mounting plate 342, on the bracket 310, and is driven by the key 322 on the drive shaft 320.

Figure 28:
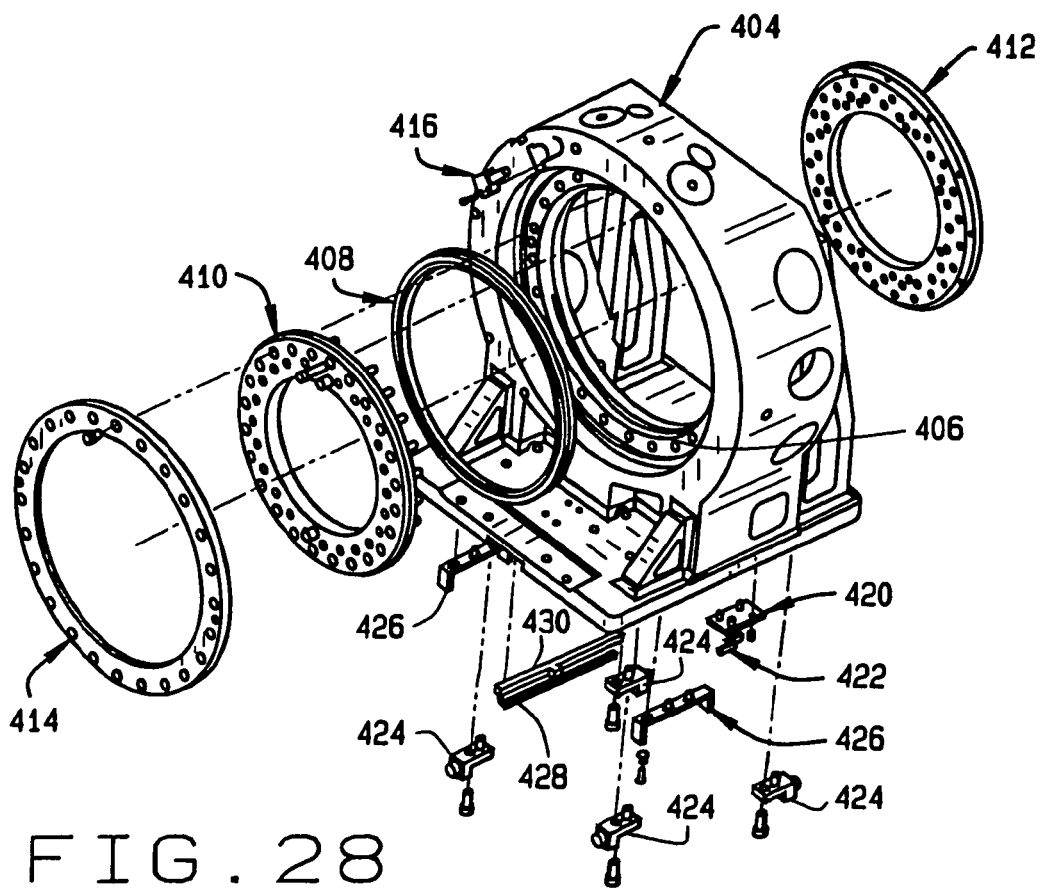
FIG. 28 is a front perspective view of the theta drive mechanism.
Figure 29:
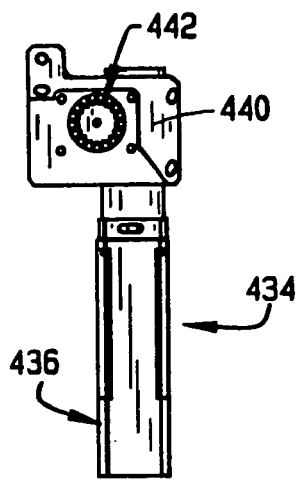
FIG. 29 is a front elevation view of theta drive motor.
Figure 30:
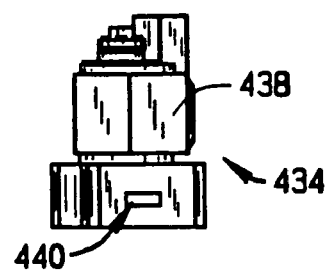
FIG. 30 is a top plan view of the theta drive motor.
Figure 31:
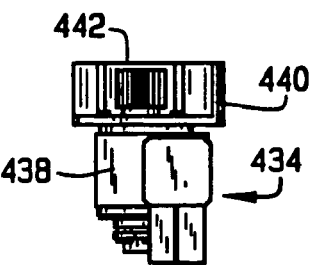
FIG. 31 is a bottom plan view of the theta drive motor.
Figure 32:
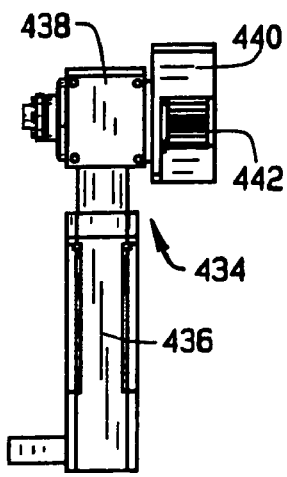
FIG. 32 is a left side elevation view of the theta motor.
Figure 33:
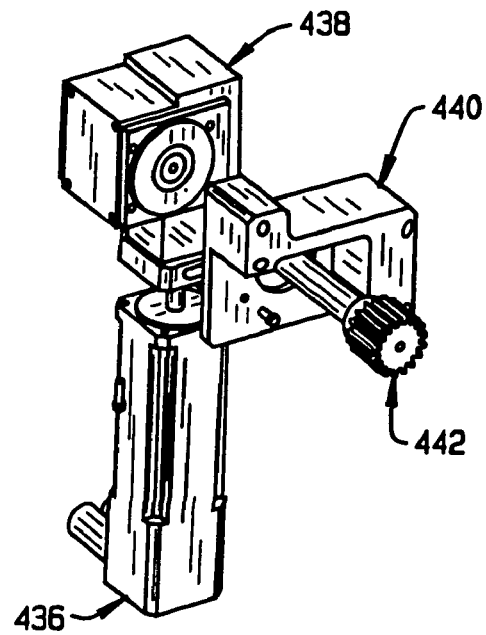
FIG. 33 is perspective view of the theta motor.
Figure 34:
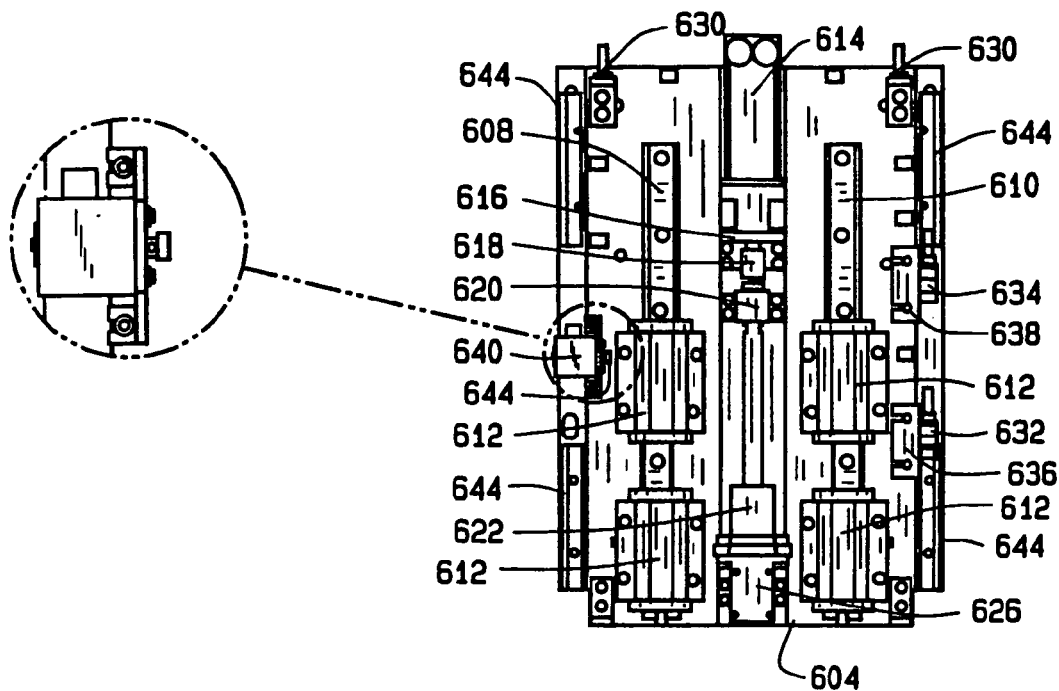
FIG. 34 is an front elevation view of the z drive mechanism.
Figure 35:
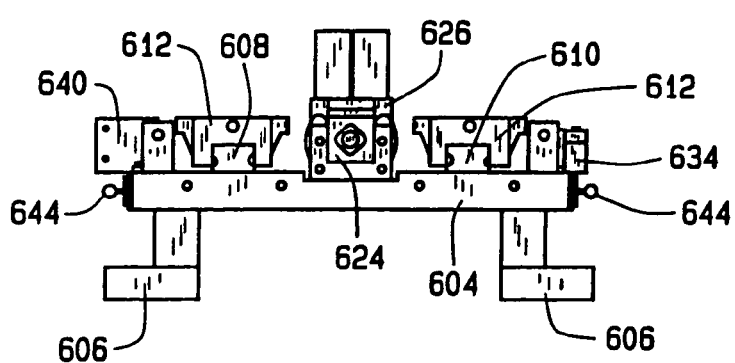
FIG. 35 is a left side elevation view of the z drive mechanism.
Figure 36:
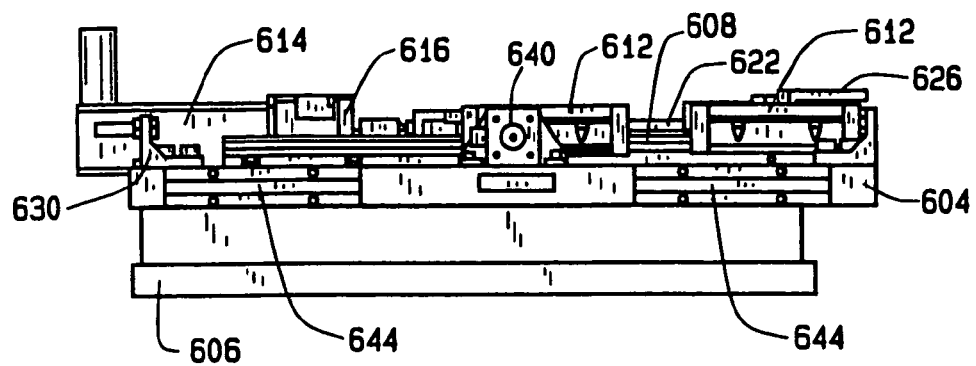
FIG. 36 is a right side elevation view of the z drive mechanism.
Figure 37:
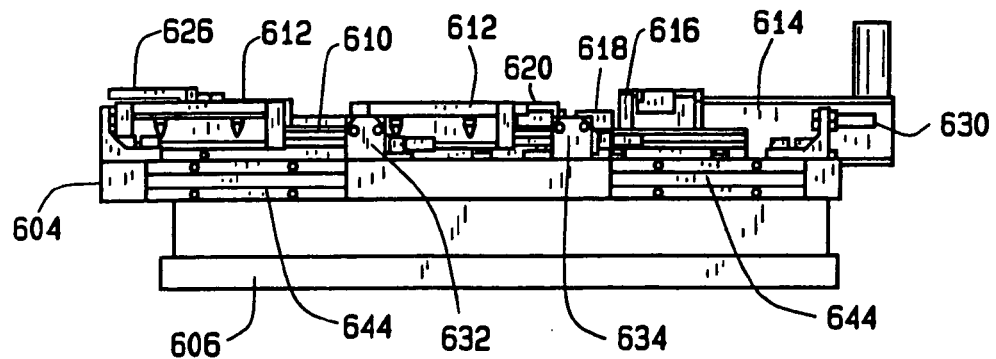
FIG. 37 is bottom plan elevation of the z drive mechanism.
Figure 38:
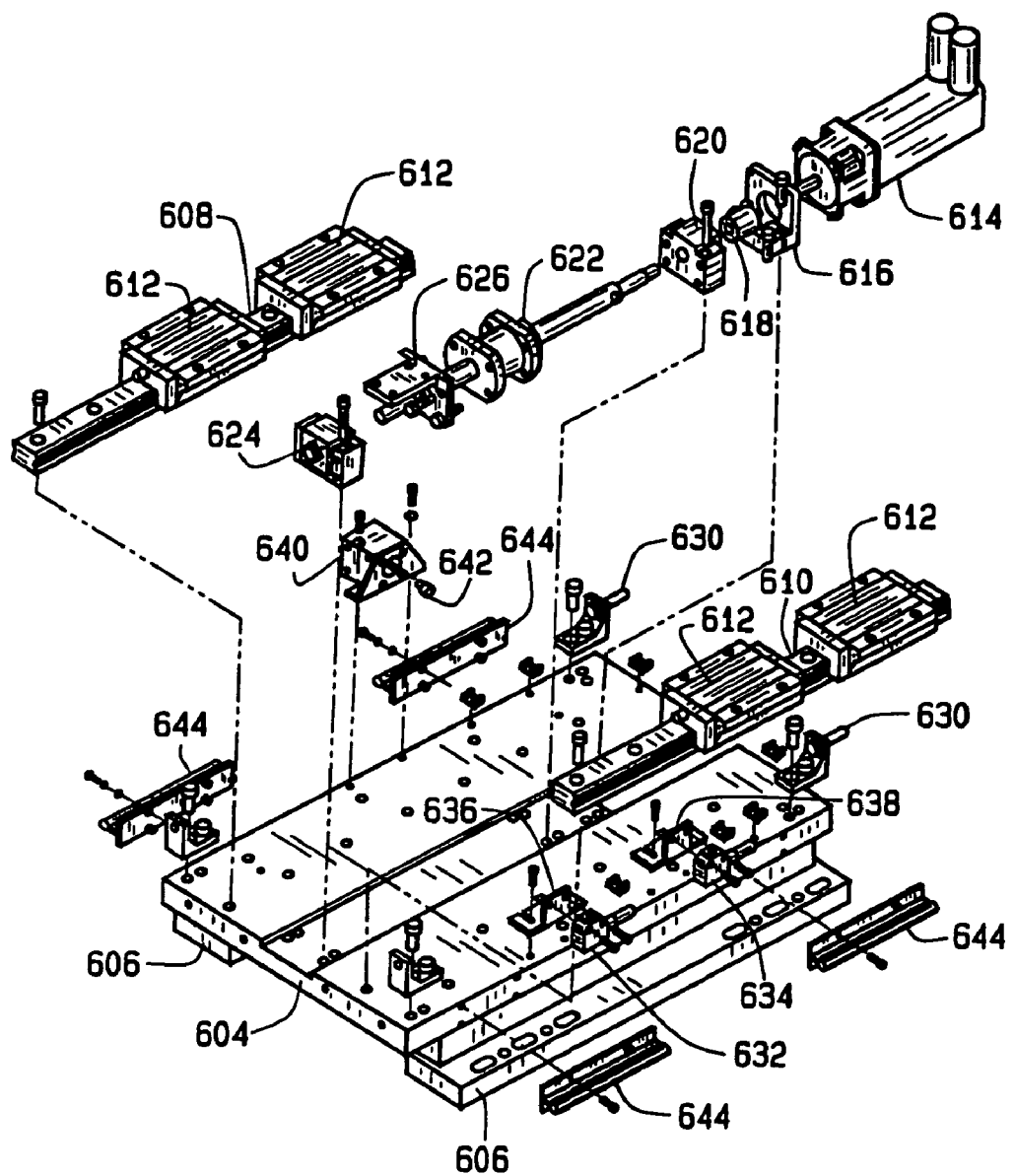
FIG. 38 is an exploded perspective view of the z drive mechanism

The $\theta$ rotation mechanism 402 is shown in FIGS. 24-28. The $\theta$ rotation mechanism 402 comprises a carriage 404, which is preferably made of aluminum or other strong, light-weight, non-magnetic material. As best shown in FIG. 28, the carriage 404 has a generally cylindrical opening 406 therein in which the outer race of a bearing 408 is mounted. Front and rear retaining hubs 410 and 412 are secured together, sandwiching the inner race of the bearing 408 between them. A retaining ring is mounted in the carriage 404 over the front retaining hub 414. The phi pivot mechanism 302 is mounted to the front retaining hub 410, for rotation around about the theta axis.

A position sensor 416 is mounted in a recess in the front of the carriage 404, and is triggered by the flag 338 on the phi pivot mechanism.

A cam tray 420, mounting a cam 422, is also secured on the bottom of the carriage 404. A plurality of stops 424 are also mounted on the bottom of the carriage 404. A pair of C-shaped brackets 426 are mounted on the bottom of the carriage for engage and moving the cover as the theta mechanism 402 moves in the z direction, as described below. A precision gear 428 is mounted on a bracket 430 on the bottom of the carriage. The precision gear is used in sensing the position in the z-direction as a back up to the position sensing built in to the z drive mechanism 602.

The driver for the $\theta$ rotation mechanism 402 is indicated generally as 434 in FIGS. 29-33. The driver 434 comprises a servo motor 436, a gear box 438, a reducer mounting plate 440, and a pinion 442. The pinion 440 engages and drives a gear 442 secured to the rear hub 444, causing rotation in the theta direction.

As shown in FIGS. 35-38, the z drive mechanism 602 comprises base plate 604. Mounting plates 606 are provided on the underside of base plate, on either side, for securing the base plate to the pedestal 800. Tracks 608 and 610 are mounted on the plate 604. Two carriages 612 are slidably mounted on each of the tracks 608 and 610, for slidably mounting the carriage 404 of the theta drive mechanism 402. A servo motor 614 is mounted on the base plate 604 with a bracket 616. A flexible shaft coupling 618, drive screw bearing 620 connect ball screw shaft 622 to the servo motor 614. The end of the ball screw shaft 622 is supported in drive screw bearing 624. A bracket 626 is mounted on the ball screw shaft 622 and is secured to the underside of the carriage 402, to move the carriage.

Stops 628 are mounted on the base plate 604 adjacent one end. Stops 630 are mounted on the base plate 604 adjacent the other end. Limit switches 632 and 634 are mounted on the plate 604 with brackets 636 an 638, respectively. A rotary encoder 640 is mounted on the base plate 604, and has a pinion 642. The pinion 642 engages the precision gear 428 on the bottom of the carriage 404, and measures the position of the carriage relative to the base plate 604. Rails 644 are mounted on the sides of the base plate 604 for slidably mounting the cover 200.

Figure 39:
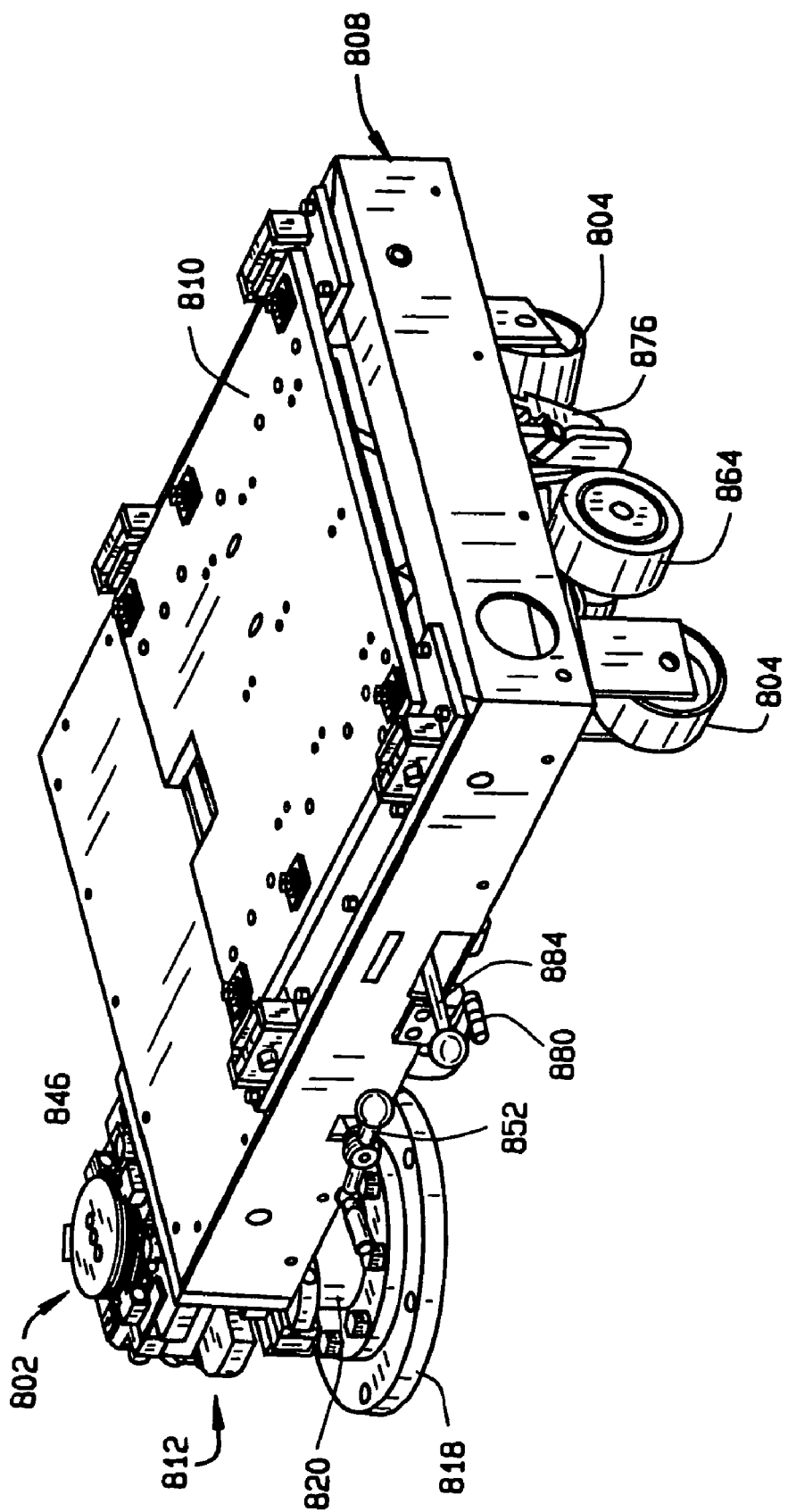
FIG. 39 is a perspective view of the pedestal.

As shown in FIG. 39, the pedestal 800 comprises a frame 808, with a platform 810 for mounting the mechanism 402. The pedestal 800 is pivotally mounted for rotation about post 402, which is secured to the floor of the operating room. A collar 812 secured to the frame 808 surrounds, and rotates around the post 402. A drive mechanism 814 is mounted in the frame 808, for driving the pedestal 800 to rotate around the post 402. A lock mechanism 816 is also mounted in the frame 808, for securing the pedestal against movement.

Figure 40:
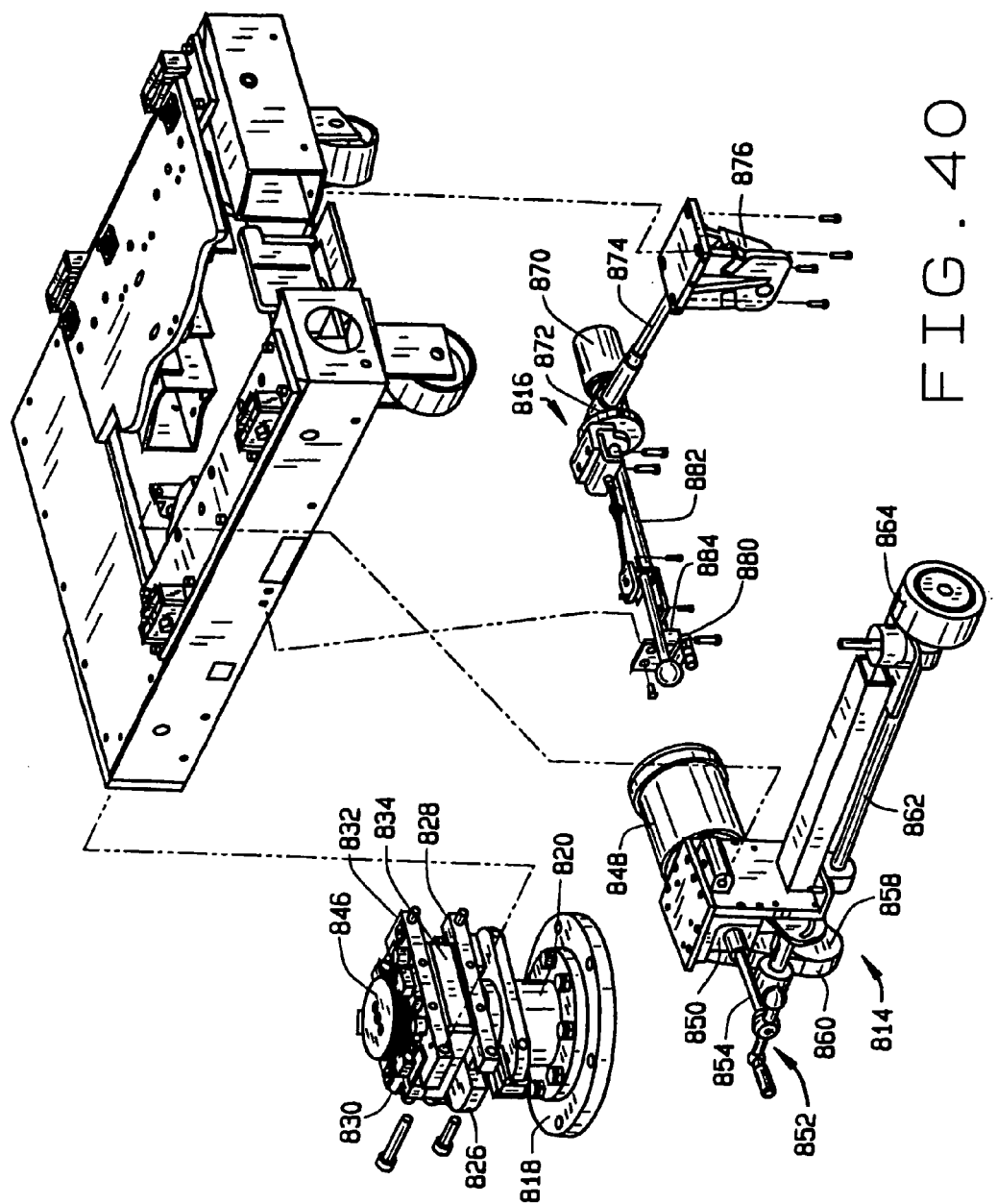
FIG. 40 is an exploded front perspective view of the pedestal showing the pivot assembly, the drive system assembly, and the locking system.
Figure 41:
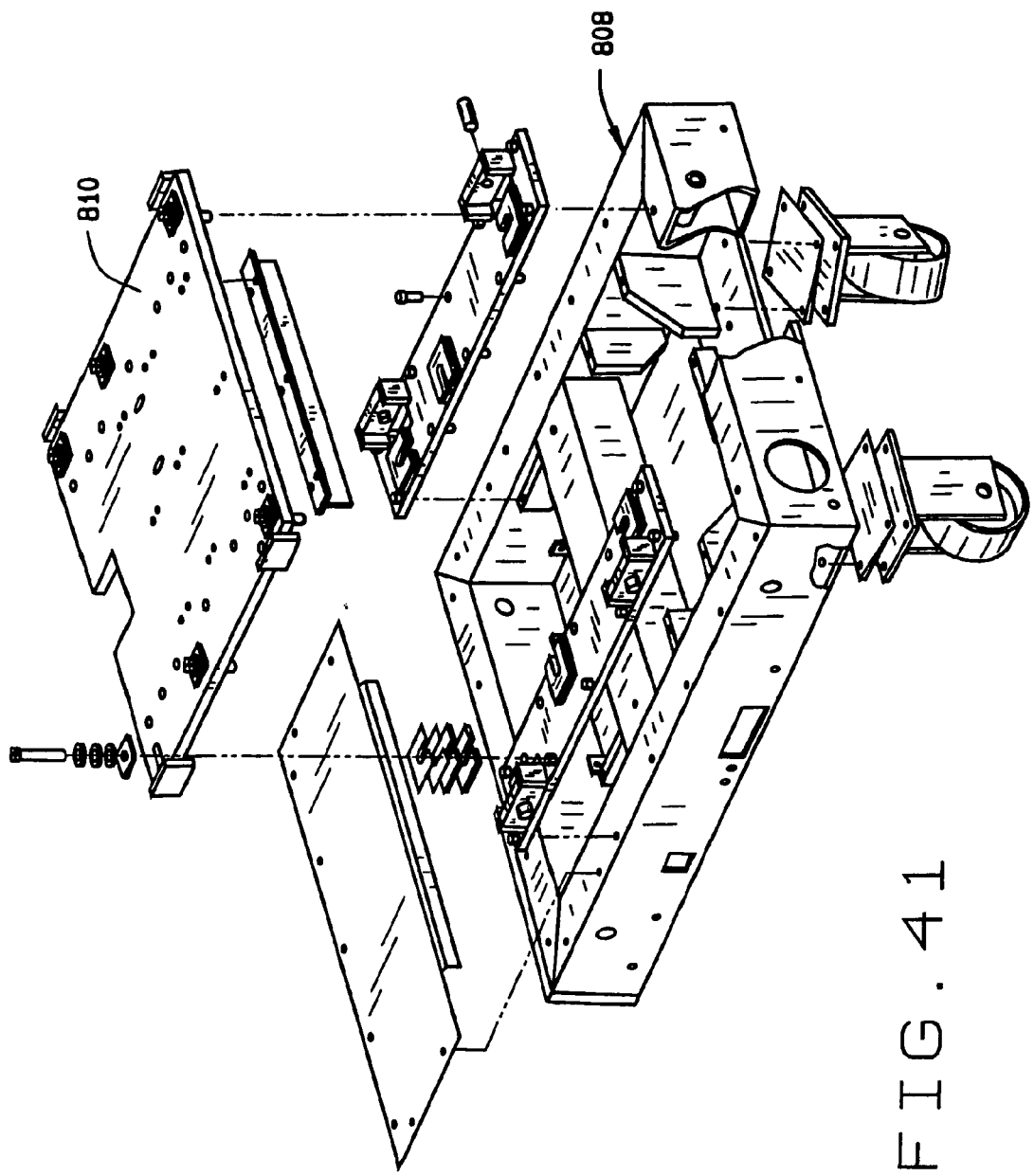
FIG. 41 is an exploded front perspective view of the pedestal with the pivot assembly, the drive system assembly, and the locking system assembly removed.
Figure 42:
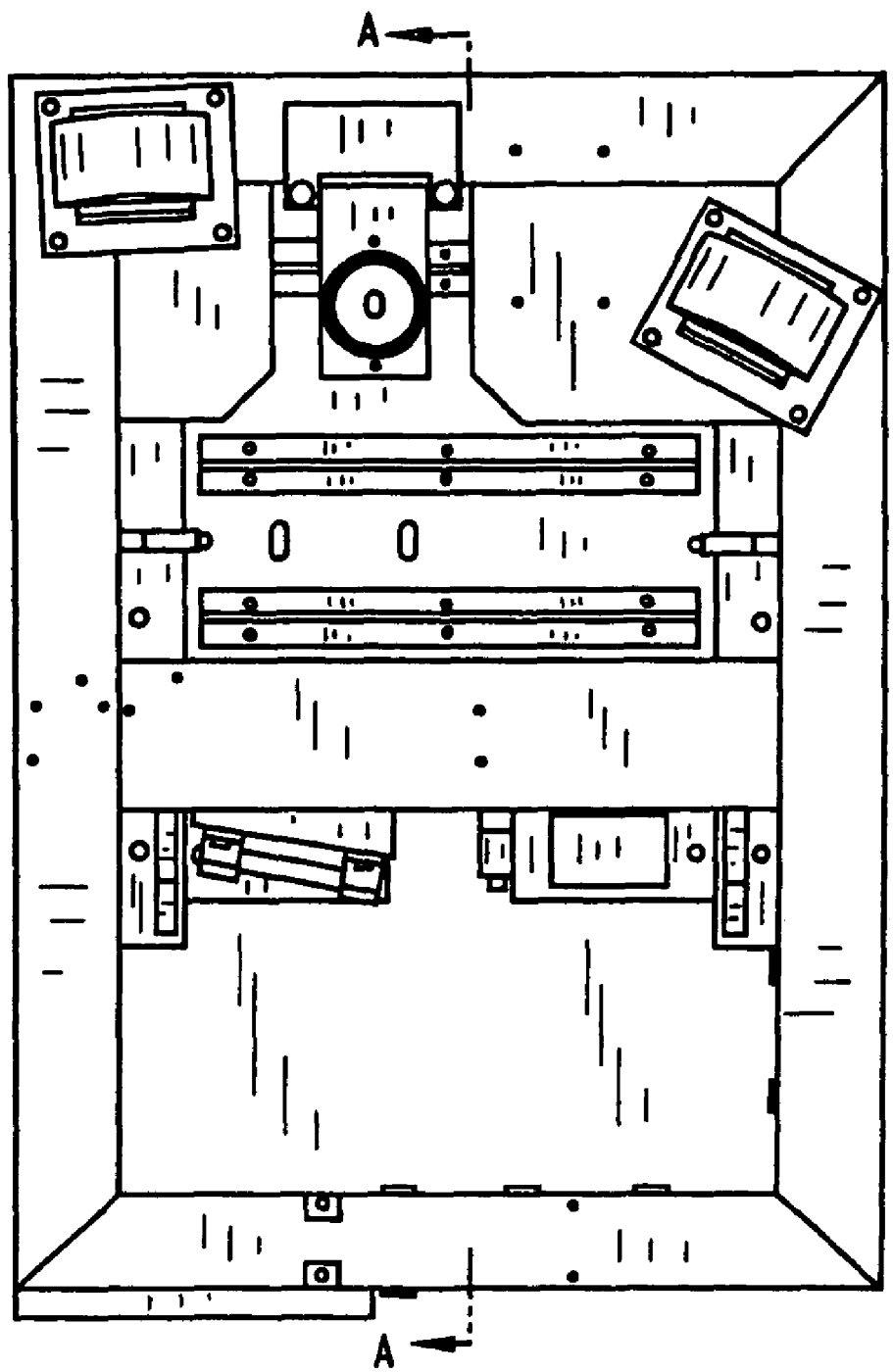
FIG. 42 is a bottom plan view of the pedestal.
Figure 43:
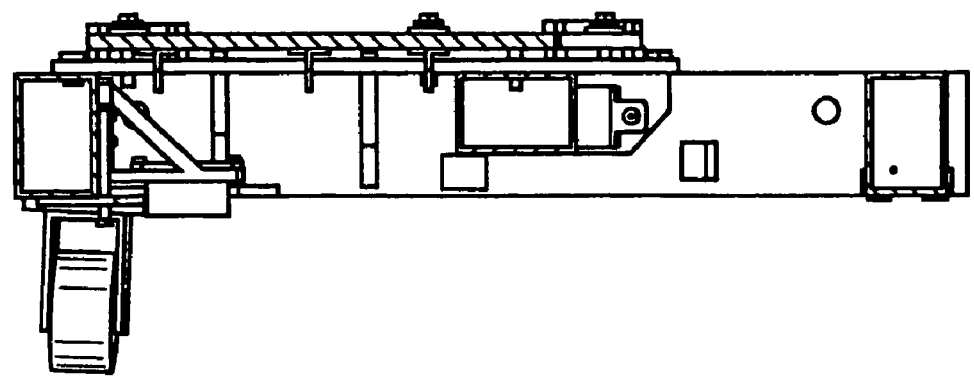
FIG. 43 is a longitudinal cross sectional view of the pedestal taken along the plane of line 43-43 in FIG. 42.
Figure 44:
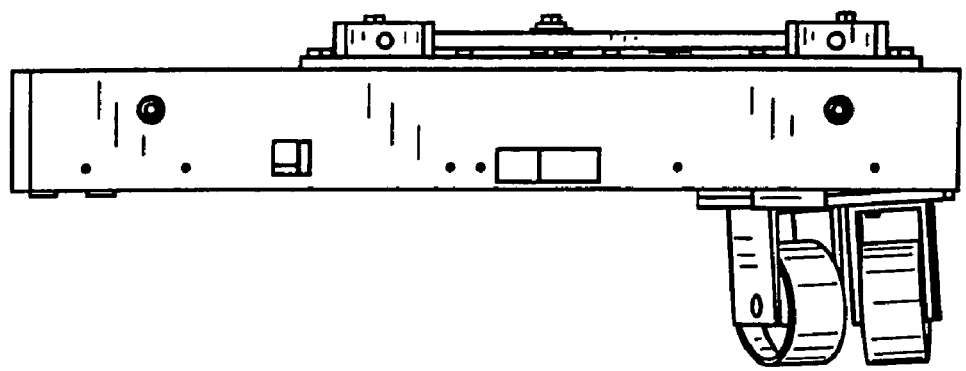
FIG. 44 is a side elevation view of the pedestal.
Figure 45:
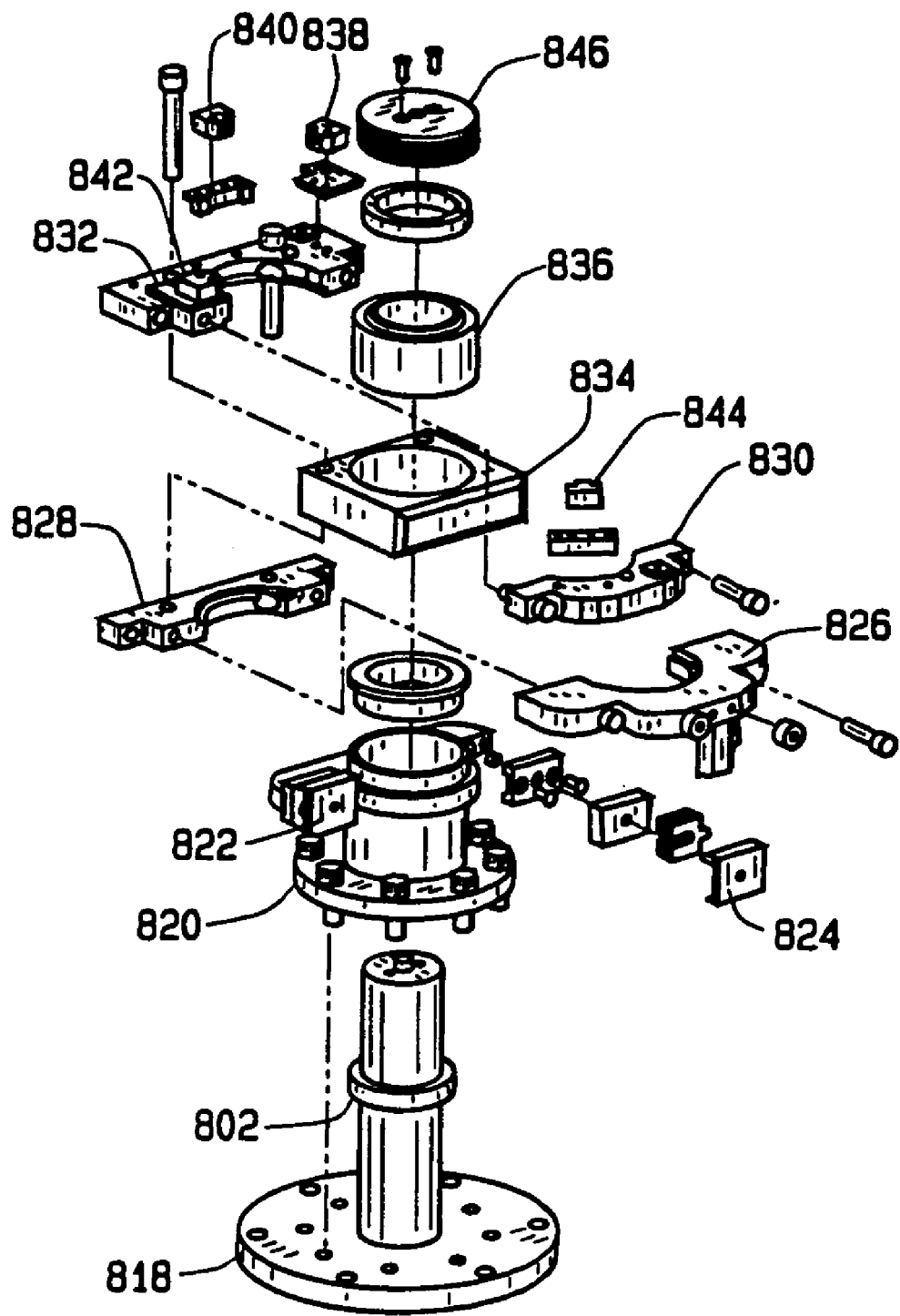
FIG. 45 is an exploded perspective view of the pivot assembly for pivotally mounting the pedestal.

As shown in FIGS. 40 and 45, the post 802 is surrounded by a weldment 818. A stop tube 820 is mounted over the post 802, providing stops 822 and 824 for limiting the rotational movement of the pedestal. Lower outer mounting plate 826 and lower inner mounting plate 828, and upper outer mounting plate 830 and upper inner mounting 832 are secured above and below block 834, mounting spherical bearing 836. Limit switches 838, 840, 842, and 844 are mounted on the upper mounting ring and are tripped by movement relative to cam 846 secured on the top of the post 802.

Figure 46:
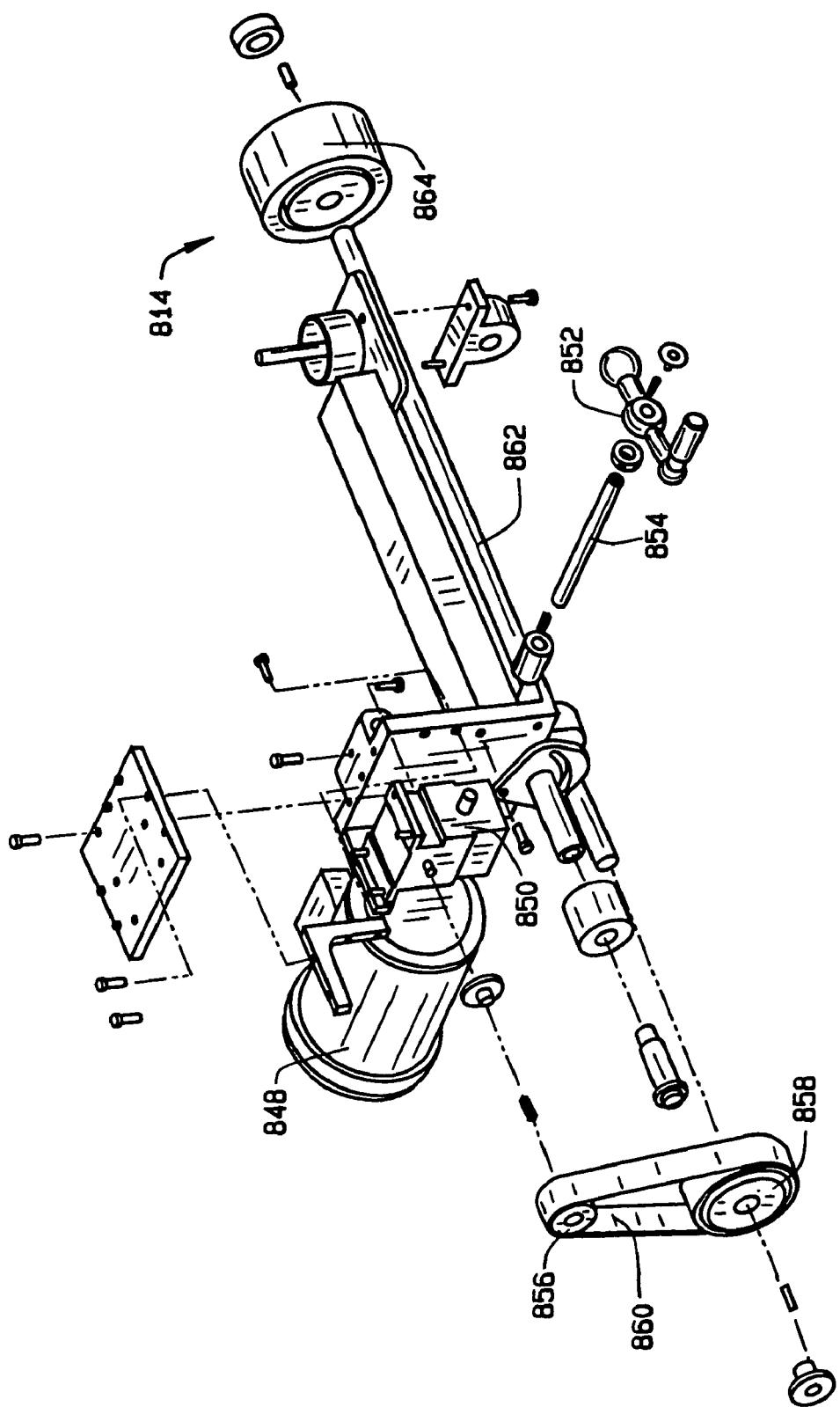
FIG. 46 is a perspective view of the drive mechanism.

As shown in FIGS. 40 and 46, the drive mechanism 814 comprises a motor 848 connected to gear box 850. A hand crank 852 on shaft 854 is also connected to gear box 850. Sheaves 856 and 858 and belt 860 connect the gear box 850 to the drives shaft 862, which in turn drives drive wheel 864. Thus the motor can operate the drive wheel, or in a situation where power is not available, hand crank 852 an be used to operate the drive wheel, and pivot the pedestal around post 802.

Figure 47:
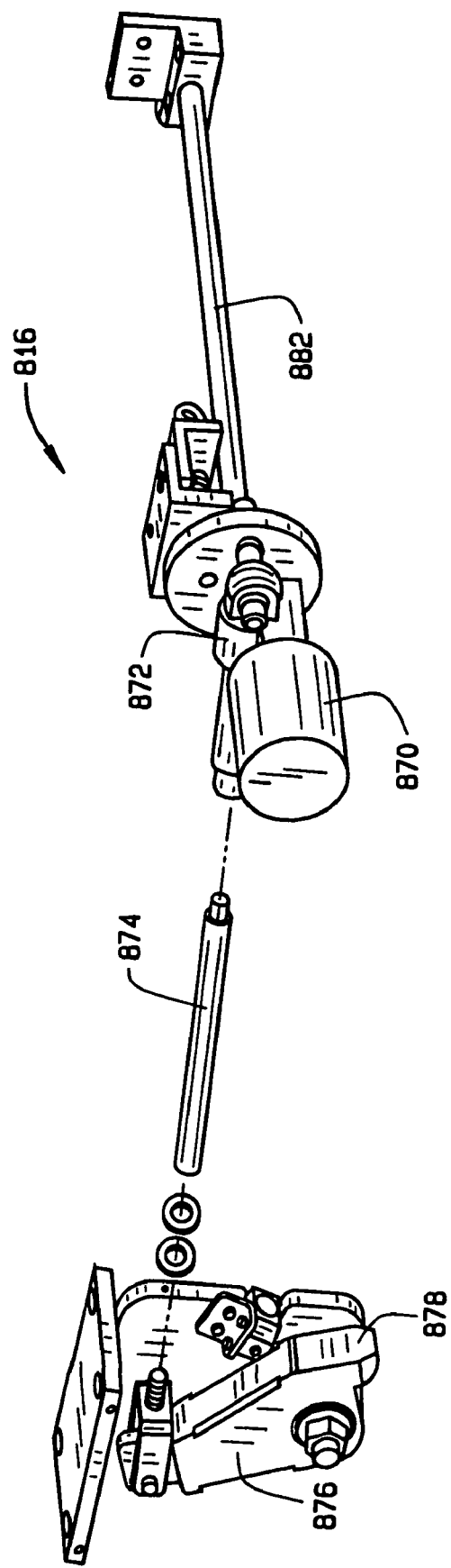
FIG. 47 is a perspective view of the drive assembly.
Figure 48:
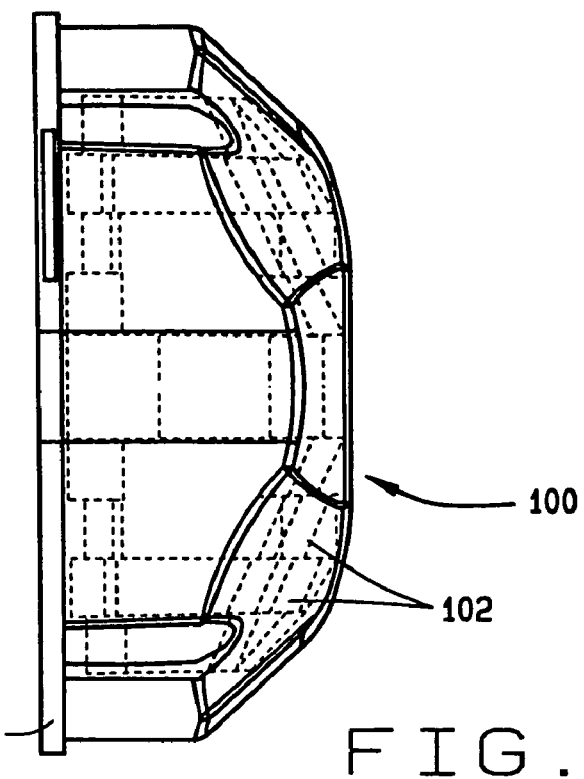
FIG. 48 is a side elevation view of the magnet.
Figure 49:
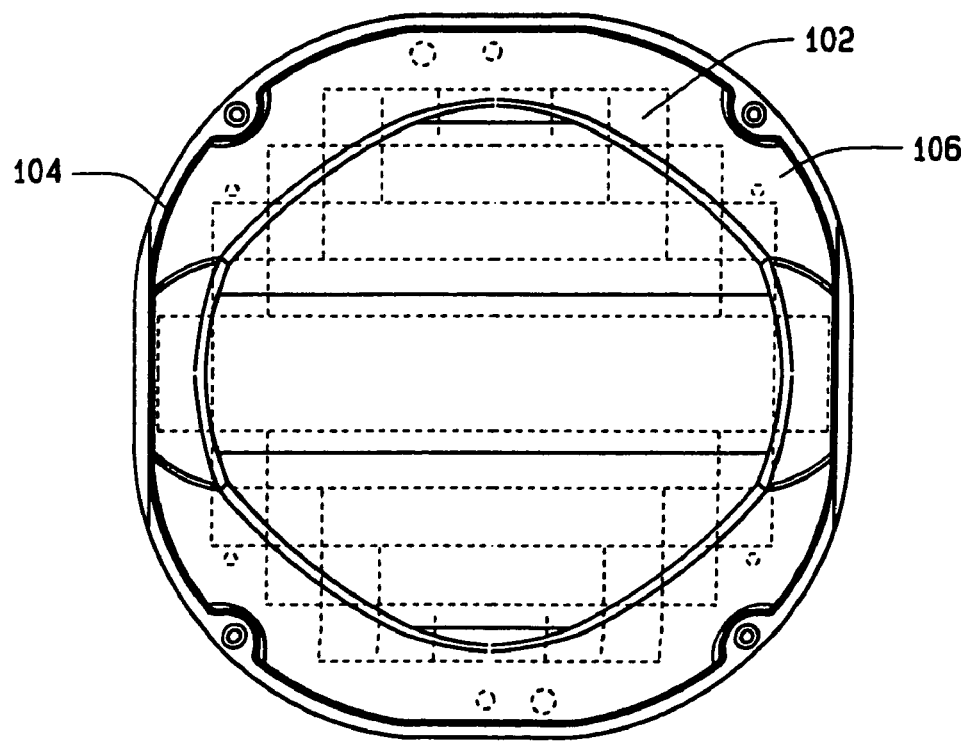
FIG. 49 is a front elevation view of the magnet.

As shown in FIGS. 40 and 47, the lock mechanism 816 comprises an electric motor 870 which turns a gear box 872 to pull or push rod 874. The pulling or pushing of the rod 874 causes the lock member 876 to pivot. The lock member 876 has a tab 878, which pivots into and engages a slot in the floor of the procedure room. A hand crank 880 on shaft 882 also turns the gear box 872, to manually pull or push rod 874. An spring biased interlock bar 884, interferes with the hand crank, and must be manipulated out of the way in order to manually operate the lock mechanism 816.

A second preferred embodiment of a magnet assembly in accordance with the principles of this invention is indicated generally as 900 and 902 in FIGS. 50-53. The magnet assemblies 900 and 902 are adapted to be mounted on opposite sides of a support to be on opposite sides of a subject on a support. The magnet assemblies 900 and 902 are similar in construction to assemblies 28 and 30 of the first embodiment, and corresponding reference numerals indicate corresponding parts through out the several views of the drawings. Like the magnet assemblies 28 and 30 of the first embodiment, the magnet assemblies 900 and 902 of the second embodiment comprise a magnet and a mechanism for moving the magnet. Also like the magnet assemblies 28 and 30, the assemblies 900 and 902 provide at least three motions to change the position and orientation of the magnets to thereby change the direction of the net magnetic field applied to the operating region in a subject on the support. More specifically, the assemblies 902 and 904 each move the magnet toward and away from the operating region (translation in the z direction); rotate the magnet about an axis parallel to the z-direction (rotation about an axis $\theta$); and pivot the magnet about an axis perpendicular to the $\theta$ axis (pivoting about an axis $\phi$. As described above, the magnets in the assemblies 900 and 902 are designed and configured that with these three motions, the magnets can provide a magnetic field in any direction in the operating region.

However, unlike the assembles 28 and 30, the assemblies 900 and 902 provide a forth movement, a rotation $\psi$ about an axis $\psi$ through the operating region, and preferably an axis parallel to the longitudinal axis of the subject and support through the operating region. In the preferred embodiment, the $\psi$ axis is the axis of the rotation of the C-arm 500. This additional movement, which is preferably coordinated, allows the magnets to move about the operating region to accommodate imaging equipment, while maintaining the generally opposed configuration of the magnets, and thereby allowing the magnet assemblies to maintain the direction and strength of the magnetic field applied to the operating region.

In this second preferred embodiment the magnet assemblies 900 and 902 permit the coordinated movement of their respective magnets about the $\psi$ axis plus and minus 15°. Of course a greater or lesser range of motion could be provided, and further the movement does not have to be coordinated, if the system control can take into account changes in the relative locations of the magnets when controlling the other three permitted motions of the magnets to achieve the desired field direction and strength.

Figure 50:
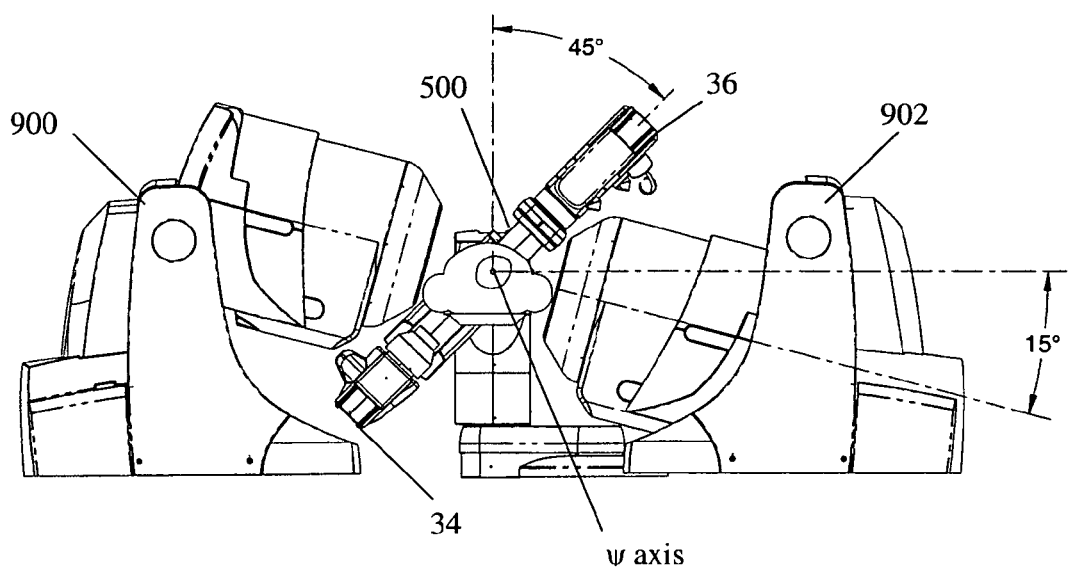
FIG. 50 is a side elevation view of the magnetic surgery suite incorporating magnet assemblies in accordance with a second preferred embodiment of this invention oriented to allow positioning of the imaging system in a maximum left anterior oblique imaging position.
Figure 51:
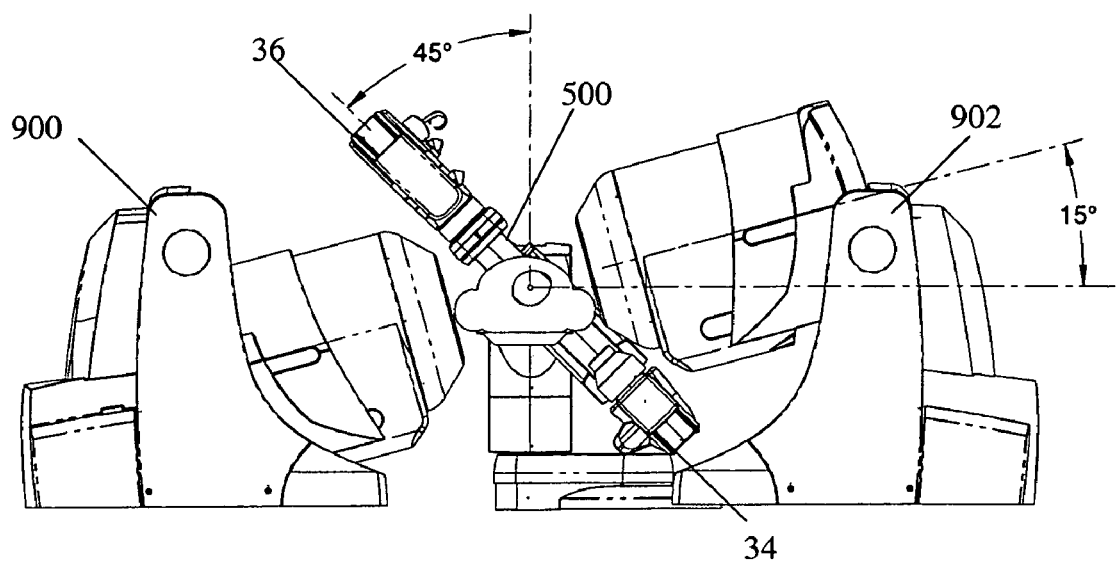
FIG. 51 is a side elevation view of the magnetic surgery suite incorporating magnet assemblies in accordance with a second preferred embodiment of this invention oriented to allow positioning of the imaging system in a maximum right anterior oblique imaging position.

As shown in FIGS. 50-51, a C-arm 500 is preferably provided for imaging the operating region in a subject on the support. The C-arm 500 rotates about an axis parallel to the longitudinal axis of the subject on the support. However, the magnet assemblies 28 and 30 of the first embodiment can sometimes interfere with imaging in certain planes, for example the Left Anterior Oblique (LAO) plane and the Right Anterior Oblique (RAO) plane, in which the x-ray source 34 and x-ray receiver 36 are oriented to image in planes 45° from horizontal, on the right and left sides of the subject. These are useful images to physicians who are familiar with and therefore comfortable working with such images. Depending on the imaging equipment and the magnets, to achieve LAO or RAO imaging it may be necessary to move the magnets out of the way of the C-arm. In the second preferred embodiment shown in FIGS. 50-53, the assemblies 900 and 902 permit coordinated movement of the magnets about the operating region (and more specifically about the $\psi$ axis) by plus or minus 15° which is sufficient to accommodate the 45° plus or minus movement of the C-arm 500.

As the magnets move because of movement of their respective magnet assemblies 900 and 902, the system controls the magnets translating them along their respective z axes, rotating them about their respective $\theta$ axes, and pivoting them about their respective $\phi$ axes to maintain the direction of the applied magnetic field in the operating region in the subject.

As shown in FIG. 50, the magnet assemblies 900 and 902 rotate their respective magnets about the $\psi$ axis to accommodate the C-arm 500 pivoting to the RAO imaging position, and as shown in FIG. 51, the magnet assemblies 900 and 902 rotate their respective magnets about the $\psi$ axis to accommodate the C-arm 500 pivoting the LAO imaging position.

Figure 52:
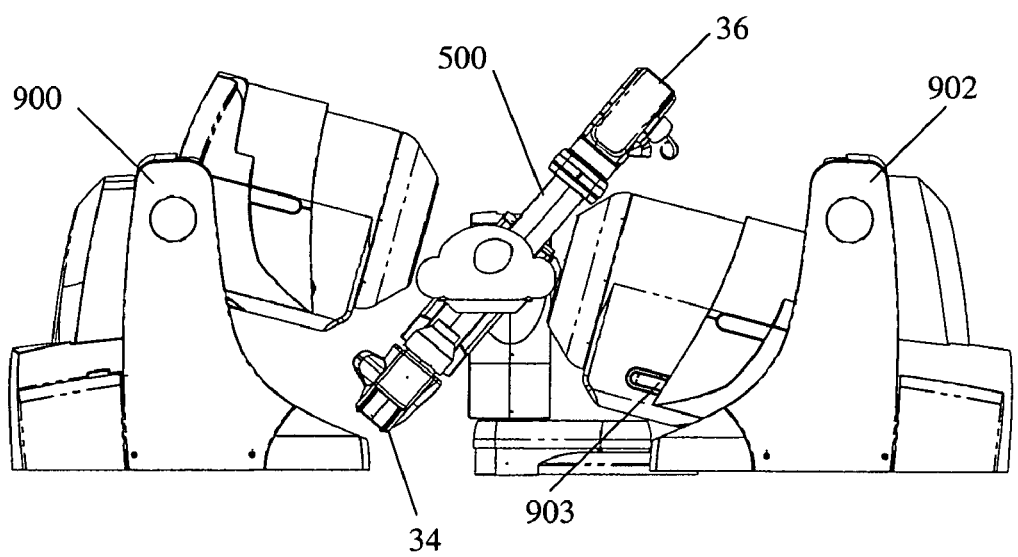
FIG. 52 is a side elevation view of the magnetic surgery suite incorporating magnet assemblies in accordance with a second preferred embodiment of this invention oriented with a maximum offset of one of the assemblies to illustrate the centering of the magnetic field on the operating region.

As shown in FIG. 52, the magnet assemblies 900 and 902 rotate their respective magnets about the $\psi$ axis to accommodate eccentric positioning of the subject on the support. Positioning the magnets rotationally around the operating region allows the magnets to be positioned more closely to the operating region than if the magnets could not be moved and remained at the sides of the subject. In the positions shown in FIG. 52, the magnets can be extended along the z-axis to be as close to the operating region as possible.

Figure 53:
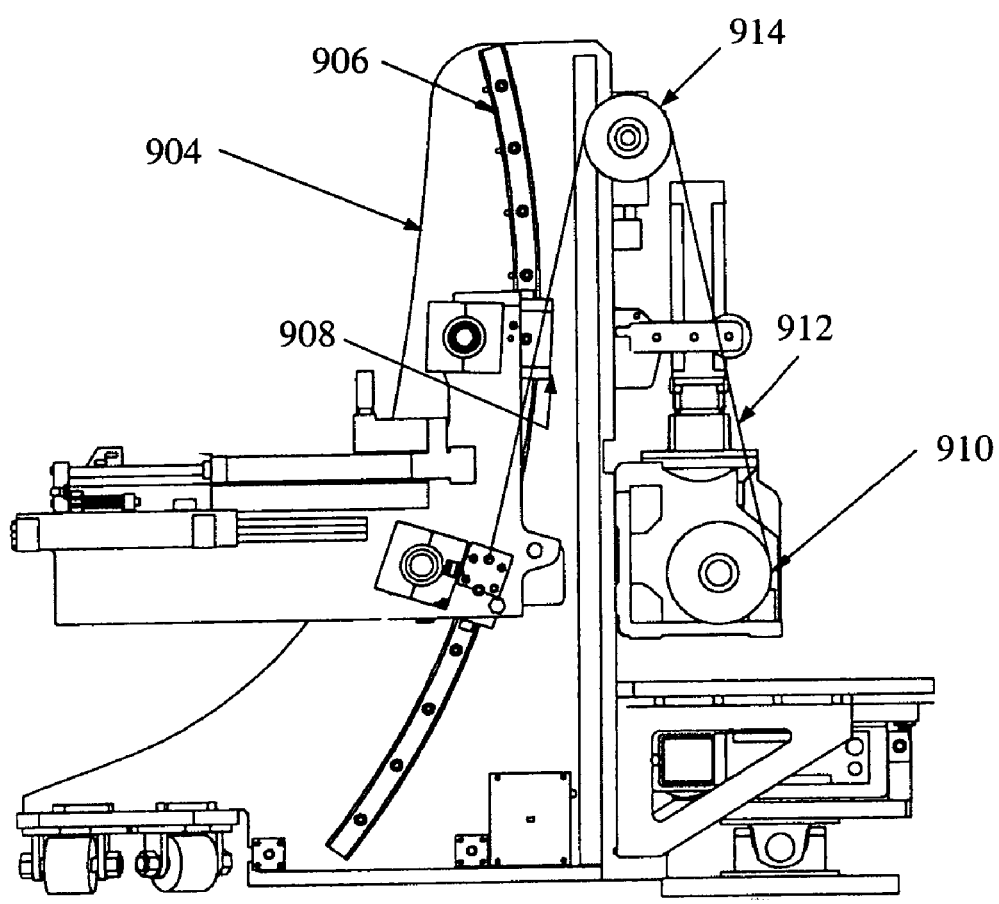
FIG. 53 is a side elevation view of the support for guiding the rotation of the magnet assemblies about the operating region.

As shown in FIG. 53, each of the magnets are carried on a carriage 904. The carriages each have mechanisms as described above with respect to magnet units 28 and 30 for moving the magnets in the z direction, rotating the magnets about the θ direction, and pivoting the magnets about the φ axis. Each of the carriages 904 has an arcuate track 906, which is preferably an arc of a circle centered at the ψ axis. Each of the carriages has rollers 908 for following the track 906. Each of the carriages 904 also has a motor driven reel 910 and a pulley 912, and a cable 914 extends from the reel 910, over the pulley 912, and is anchored on the carriage 904. As the reel 910 winds the cable 914, the carriage 904 is pulled upwardly along the track 906, and as the reel 910 unwinds the cable 914, the carriage is lowered along the track 906.

The magnet assemblies 900 and 902 are preferably controlled so that as the carriage 904 on assembly 900 is raised the carriage 904 on assembly 902 is lowered. Thus the magnets of the two assemblies on substantially opposing sides of the operating region. In operation the magnet assemblies 900 and 902 are typically operated with their carriages in a level position, as shown in FIG. 53. When the physician calls for an RAO view, the magnet assemblies 900 and 902 are operated so that carriage 904 of magnet assembly 900 raises, and the carriage 904 of assembly 902 lowers to accommodate the rotation of the C-arm 500 to the RAO position. Similarly, when the physician calls for an LAO view, the magnet assemblies 900 and 902 are operated so that carriage 904 of magnet assembly 900 lowers, and the carriage 904 of assembly 902 raises to accommodate the rotation of the C-arm 500 to the LAO position.

The above described improvements and advantages of the second preferred embodiment should be readily apparent to one skilled in the art, as to enabling a full range of X-ray imaging while maintaining continuous magnetic navigation capability. It should be noted that the control of the magnet units 28 and 30 of the navigation system and other various movement controls could be controlled by a user input from an input device such as a joystick, mouse, or hand-held localized stylus, or it could automatically be controlled by a computer. Additional design considerations such as the above improvement in maintaining a desired magnetic field direction throughout a rotation range of a magnet unit may be incorporated without departing from the spirit and scope of the invention. Likewise, a variety of medical devices such as catheters, cannulas, guidewires, microcatheters, endoscopes and others known to those skilled in the art can be remotely guided according to the principles taught herein. Accordingly, it is not intended that the invention be limited by the particular form described above, but by the appended claims.

What is claimed is:

1. A system for magnetically navigating a medical device in an operating region within the body of a patient, the system comprising:

two or more magnets each having a magnetic field projecting from the front of the magnet, which collectively are sufficient to apply a magnetic field of a selected direction in an operating region in the patient;

a magnet support for each of the two or more magnets, the magnet supports being pivotable between an active position near the patient and an inactive position away from the patient, each of the two or more magnetics being rotatable about the patient to maintain the magnitude of the magnetic field, and further being capable of translation towards or away from the patient to allow the two or more magnets to be centered around the operating region of the patient, the two or more magnets being movable between a first position of maximum clockwise rotation about the patient and a second position of maximum counterclockwise rotation about the patient; and an X-ray imaging system proximate to the two or more magnets, the X-ray imaging system being capable of a predetermined range of rotation about the patient to provide X-ray images of the operating region concurrent with operation of the two or more magnets, wherein the rotation of the two or more magnets to a maximum position interferes with the range of rotation of the imaging system in at least one maximum position.

2. A magnet system for applying a magnetic field of selected direction to an operating region inside a patient on a support, to control a magnetic medical object in the operating region, the magnet system comprising:

two or more magnets, each on a magnet support, and each being movable with respect to its magnet support to rotate about the patient between first and second maximum positions to control the direction of a magnetic field for controlling the magnetic medical object in the operating region in the patient, and each being capable of translation towards or away from the patient to allow the two or more magnets to be centered around the operating region of the patient, the magnet supports being mounted on a pivoting base so that the magnet supports can be moved between active and inactive positions by the pivoting of the base, an X-ray imaging system proximate to the two or more magnets, the X-ray imaging system having a range of movement about the patient to obtain X-ray images of the operating region; and wherein the two or more magnets can be rotated about the patient to prevent obstruction of the imaging system's range of movement, while maintaining the magnitude of the magnetic field in a selected direction in the operating region, the rotation of the two or more magnets to a maximum position interfering with the range of rotation of the imaging system in at least one maximum position.

3. A magnet system for applying a magnetic field of selected direction to an operating region within the body of a patient, the magnet system comprising two or more magnets;

a support for mounting each of the two or more magnets, the supports being movable to rotate the two or more magnets between first and second maximums about the patient for changing the position and orientation of the two or more magnets to change the direction of the magnetic field applied to the operating region, wherein the supports are moveable for rotating each of the two or more magnets about a first axis that rotates about a second axis perpendicular to the first axis, and translating each of the two or more magnets towards or away from the patient, the two or more magnet supports being mounted on a pivoting base, such that the magnet supports may be moved between an active and inactive position by the pivoting of the base; and an X-ray imaging system capable of a range of rotation about the patient and within the space between the two or more magnets, wherein the two or more magnets may be rotated to provide for an increased range of rotation for the X-ray imaging system while also maintaining the magnitude of the applied magnetic field
wherein the two or more magnets are further capable of translation towards or away from the patient to allow the two or more magnets to be centered around the operating region of the patient, and wherein the rotation of the two or more magnets to a maximum position interferes with the range of rotation of the imaging system in at least one maximum position.

4. A magnet system for applying a magnetic field of selected direction to an operating region within the body of a patient, the magnet system comprising:
an X-ray imaging system comprising a range of movement about the patient to obtain X-ray images of the operating region;
two or more magnets sufficient for applying a magnetic field in a selected direction in the operating region of a patient:
a support for mounting each of the two or more magnets, the supports being movable to rotate the one or more magnets about the patient between first and second maximums to change the position and orientation of the magnets to change the direction of magnetic field applied to the operating region in the patient, the magnets being movable between a first maximum rotation position in which the imaging system may be moved to face the left side of the patient, and a second maximum rotation position in which the imaging system may be moved to face the right side of the patient; the two or more magnets being configured to maintain the magnitude of the magnetic field applied in a selected direction at any point of rotation between the first and second maximum rotation positions; the two or more magnets further being capable of translation towards or away from the patient to allow the two or more magnets to be centered around the operating region of the patient;
the supports being mounted on a pivoting base so that the supports may be moved between an active and inactive position by the pivoting of the base wherein the rotation of the two or more magnets to a maximum position interferes with the range of rotation of the imaging system in at least one maximum position.

5. A magnet system for applying a magnetic field of a selected direction to a region within a subject body, the magnet system comprising:
an X-ray imaging system having a range of movement about the patient to obtain X-ray images of the region;
a plurality of supports, each of which provides for a mounting of a magnet that permits rotation of the magnet about the support;
at least one magnet on each support configured to apply a magnetic field of a selected direction while moving relative to the support between a first position and second position of maximum rotation about the subject body; and
wherein the plurality of supports are movable to rotate the magnets about the patient while maintaining the selected magnetic field direction while being moveable to provide clearance for the X-ray imaging system to move about the patient, such that the X-ray imaging system can obtain images of the subject body from any position in its range of movement concurrent with the operation of the magnets on the plurality of supports.

6. The magnet system of claim 5, wherein the plurality of supports are further movable to translate towards the patient to allow the magnets on the plurality of supports to be centered around the operating region of the patient.

7. The magnet system of claim 6, wherein the range of movement of the magnets on the plurality of supports between maximum positions interferes with the range of rotation of the imaging system.

8. The magnet system of claim 7, wherein the plurality of magnet supports are mounted on a pivoting base, and wherein the magnet supports are movable between an active and inactive position by pivoting of the base.

9. The magnet system of claim 8, further comprising a curved rail on each of the plurality of supports, wherein the magnets on the plurality of supports are mounted to the curved rail to permit movement of the magnets along to the rail for providing rotation about the patient.

* * * * *